US005811288A

United States Patent [19]

Sabe

[11] Patent Number: 5,811,288

[45] Date of Patent: Sep. 22, 1998

[54] ISOFORM GENE FOR FOCAL ADHESION PROTEIN PAXILLIN

[75] Inventor: Hisataka Sabe, Osaka, Japan

[73] Assignee: Japan Science and Technology Corporation, Saitama, Japan

[21] Appl. No.: 889,402

[22] Filed: Jul. 8, 1997

[30] Foreign Application Priority Data

Jul. 8, 1996 [JP] Japan .................................... 8-178334

[51] Int. Cl.[6] .............................. C12N 1/21; C12N 15/70

[52] U.S. Cl. .................................. 435/252.33; 435/320.1; 436/540; 530/352; 536/23.4; 536/23.5

[58] Field of Search ............................ 435/252.33, 320.1; 436/540; 530/352; 536/23.4, 23.5

[56] References Cited

PUBLICATIONS

Salgia et al., *J. Biol. Chem*, vol. 270, 1995, pp. 5039–5047.

*Primary Examiner*—James Ketter
*Attorney, Agent, or Firm*—Clifford M. Davidson

[57] ABSTRACT

Described are cloning and sequencing of genes encoding novel isoforms (paxillins β and γ) of focal adhesion protein paxillin. According to the present invention, there is provided a novel gene for an isoform of focal adhesion protein paxillin. This gene is useful medical applications such as diagnosis of progress of cancer malignancy, development of a drug (cancer treatment) for preventing the metastasis and infiltration of cancer cells, etc.

19 Claims, 25 Drawing Sheets

FIG. 1A

```
1/1                                     31/11
atg gac gac ctc gac gcc ctg ctg gcg gac ttg gag tct acc acc tcc cac atc tcc aaa
Met asp asp leu asp ala leu leu ala asp leu glu ser thr thr ser his ile ser lys
61/21                                   91/31
cgg cct gtg ttc ttg tcg gag gag acc ccc tac tca tac cca act gga aac cac aca tac
arg pro val phe leu ser glu glu thr pro tyr ser tyr pro thr gly asn his thr tyr
121/41                                  151/51
cag gag att gcc gtg cca ccc ccc gtc ccc cca ccc ccg tcc agc gag gcc ctc aat ggc
gln glu ile ala val pro pro pro val pro pro pro pro ser ser glu ala leu asn gly
181/61                                  211/71
aca atc ctt gac ccc tta gac cag tgg cag ccc agc ggc tcc cga ttc atc cac cag cag
thr ile leu asp pro leu asp gln trp gln pro ser gly ser arg phe ile his gln gln
241/81                                  271/91
cct cag tcc tca tca cct gtg tac ggc tcc agt gcc aaa act tcc agt gtc tcc aac cct
pro gln ser ser ser pro val tyr gly ser ser ala lys thr ser ser val ser asn pro
301/101                                 331/111
cag gac agt gtt ggc tct ccg tgc tcc cga gtg ggt gag gag gag cac gtc tac agc ttc
gln asp ser val gly ser pro cys ser arg val gly glu glu glu his val tyr ser phe
```

FIG. 1B

```
361/121                                 391/131
ccc aac aag cag aaa tca gct gag cct tca ccc acc gta atg agc acg tcc ctg ggc agc
pro asn lys gln lys ser ala glu pro ser pro thr val met ser thr ser leu gly ser
421/141                                 451/151
aac ctt tct gaa ctc gac cgc ctg ctg ctg gaa ctg aac gct gta cag cat aac ccg cca
asn leu ser glu leu asp arg leu leu leu glu leu asn ala val gln his asn pro pro
481/161                                 511/171
ggc ttc cct gca gat gag gcc aac tca agc ccc ccg ctt cct ggg gcc ctg agc ccc ctc
gly phe pro ala asp glu ala asn ser ser pro pro leu pro gly ala leu ser pro leu
541/181                                 571/191
tat ggt gtc cca gag act aac agc ccc ttg gga ggc aaa gct ggg ccc ctg acg aaa gag
tyr gly val pro glu thr asn ser pro leu gly gly lys ala gly pro leu thr lys glu
601/201                                 631/211
aag cct aag cgg aat ggg ggc cgg ggc ctg gag gac gtg cgg ccc agt gtg gag agt ctc
lys pro lys arg asn gly gly arg gly leu glu asp val arg pro ser val glu ser leu
661/221                                 691/231
ttg gat gaa ctg gag agc tcc gtg ccc agc ccc gtc cct gcc atc act gtg aac cag ggc
leu asp glu leu glu ser ser val pro ser pro val pro ala ile thr val asn gln gly
```

FIG. 1C

```
721/241                                        751/251
gag atg agc agc ccg cag cgc gtc acc tcc acc caa cag cag aca cgc atc tcg gcc tcc
glu met ser ser pro gln arg val thr ser thr gln gln gln thr arg ile ser ala ser
781/261                                        811/271                  β — SPECIFIC SEQUENCE →
tct gcc acc agg gag ctg gac gag ctg atg gct tcg ctg tcg gat ttc aag | atc cag gac
ser ala thr arg glu leu asp glu leu met ala ser leu ser asp phe lys | ile gln asp
841/281                                        871/291
ctg gag caa aga gcg gat ggg gag cgg tgc tgg gcg gcc ggc tgg cct cgg gac ggc ggg
leu glu gln arg ala asp gly glu arg cys trp ala ala gly trp pro arg asp gly gly
901/301                                        931/311
cgg agc agc ccc gga ggg cag gac gag gga ggg | ttc atg gcc cag ggg aag aca ggg agc
arg ser ser pro gly gly gln asp glu gly gly | phe met ala gln gly lys thr gly ser
961/321                                        991/331
agc tca ccc cct ggg ggg ccc ccg aag ccc ggg agc cag ctg gac agc atg ctg ggg agc
ser ser pro pro gly gly pro pro lys pro gly ser gln leu asp ser met leu gly ser
1021/341                                       1051/351
ctg cag tct gac ctg aac aag ctg ggg gtc gcc aca gtc gcc aaa gga gtc tgc ggg gcc
leu gln ser asp leu asn lys leu gly val ala thr val ala lys gly val cys gly ala
1081/361                                       1111/371
```

FIG. 2A

```
tgc aag aag ccc atc gcc ggg cag gtt gtg acc gcc atg ggg aag acg tgg cac ccc gag
cys lys lys pro ile ala gly gln val val thr ala met gly lys thr trp his pro glu
1141/381                                1171/391
cac ttc gtc tgc acc cac tgc cag gag gag atc gga tcc cgg aac ttc ttc gag cgg gat
his phe val cys thr his cys gln glu glu ile gly ser arg asn phe phe glu arg asp
1201/401                                1231/411
gga cag ccc tac tgt gaa aag gac tac cac aac ctc ttc tcc ccg cgc tgc tac tac tgc
gly gln pro tyr cys glu lys asp tyr his asn leu phe ser pro arg cys tyr tyr cys
1261/421                                1291/431
aac ggc ccc atc ctg gat aaa gtg gtg aca gcc ctt gac cgg acg tgg cac cct gaa cac
asn gly pro ile leu asp lys val val thr ala leu asp arg thr trp his pro glu his
1321/441                                1351/451
ttc ttc tgt gca cag tgt gga gcc ttc ttt ggt ccc gaa ggg ttc cac gag aag gac ggc
phe phe cys ala gln cys gly ala phe phe gly pro glu gly phe his glu lys asp gly

1381/461                                1411/471
aag gcc tac tgt cgc aag gac tac ttc gac atg ttc gca ccc aag tgt ggc ggc tgc gcc
lys ala tyr cys arg lys asp tyr phe asp met phe ala pro lys cys gly gly cys ala
```

FIG. 2B

```
1441/481                                1471/491
cgg gcc atc ctg gag aac tat atc tca gcc ctc aac acg ctg tgg cat cct gag tgc ttt
arg ala ile leu glu asn tyr ile ser ala leu asn thr leu trp his pro glu cys phe
1501/501                                1531/511
gtg tgc cgg gaa tgc ttc acg cca ttc gtg aac ggc agc ttc ttc gag cac gac ggg cag
val cys arg glu cys phe thr pro phe val asn gly ser phe phe glu his asp gly gln
1561/521                                1591/531
ccc tac tgt gag gtg cac tac cac gag cgg cgc ggc tcg ctg tgt tct ggc tgc cag aag
pro tyr cys glu val his tyr his glu arg arg gly ser leu cys ser gly cys gln lys
1621/541                                1651/551
ccc atc acc ggc cgc tgc atc acc gcc atg gcc aag aag ttc cac ccc gag cac ttc gtc
pro ile thr gly arg cys ile thr ala met ala lys lys phe his pro glu his phe val
1681/561                                1711/571
tgt gcc ttc tgc ctc aag cag ctc aac aag ggc acc ttc aag gag cag aac gac aag cct
cys ala phe cys leu lys gln leu asn lys gly thr phe lys glu gln asn asp lys pro
1741/581                                1771/591
tac tgt cag aac tgc ttc ctc aag ctc ttc tgc tag
tyr cys gln asn cys phe leu lys leu phe cys AMB
```

FIG.3A

```
1/1                                     31/11
atg gac gac ctc gac gcc ctg ctg gcg gac ttg gag tct acc acc tcc cac atc tcc aaa
Met asp asp leu asp ala leu leu ala asp leu glu ser thr thr ser his ile ser lys
61/21                                   91/31
cgg cct gtg ttc ttg tcg gag gag acc ccc tac tca tac cca act gga aac cac aca tac
arg pro val phe leu ser glu glu thr pro tyr ser tyr pro thr gly asn his thr tyr
121/41                                  151/51
cag gag att gcc gtg cca ccc ccc gtc ccc cca ccc ccg tcc agc gag gcc ctc aat ggc
gln glu ile ala val pro pro pro val pro pro pro pro ser ser glu ala leu asn gly
181/61                                  211/71
aca atc ctt gac ccc tta gac cag tgg cag ccc agc ggc tcc cga ttc atc cac cag cag
thr ile leu asp pro leu asp gln trp gln pro ser gly ser arg phe ile his gln gln
241/81                                  271/91
cct cag tcc tca tca cct gtg tac ggc tcc agt gcc aaa act tcc agt gtc tcc aac cct
pro gln ser ser ser pro val tyr gly ser ser ala lys thr ser ser val ser asn pro
301/101                                 331/111
cag gac agt gtt ggc tct ccg tgc tcc cga gtg ggt gag gag gag cac gtc tac agc ttc
gln asp ser val gly ser pro cys ser arg val gly glu glu glu his val tyr ser phe
```

FIG.3B

```
361/121                                 391/131
ccc aac aag cag aaa tca gct gag cct tca ccc acc gta atg agc acg tcc ctg ggc agc
pro asn lys gln lys ser ala glu pro ser pro thr val met ser thr ser leu gly ser
421/141                                 451/151
aac ctt tct gaa ctc gac cgc ctg ctg ctg gaa ctg aac gct gta cag cat aac ccg cca
asn leu ser glu leu asp arg leu leu leu glu leu asn ala val gln his asn pro pro
481/161                                 511/171
ggc ttc cct gca gat gag gcc aac tca agc ccc ccg ctt cct ggg gcc ctg agc ccc ctc
gly phe pro ala asp glu ala asn ser ser pro pro leu pro gly ala leu ser pro leu
541/181                                 571/191
tat ggt gtc cca gag act aac agc ccc ttg gga ggc aaa gct ggg ccc ctg acg aaa gag
tyr gly val pro glu thr asn ser pro leu gly gly lys ala gly pro leu thr lys glu
601/201                                 631/211
aag cct aag cgg aat ggg ggc cgg ggc ctg gag gac gtg cgg ccc agt gtg gag agt ctc
lys pro lys arg asn gly gly arg gly leu glu asp val arg pro ser val glu ser leu
661/221                                 691/231
ttg gat gaa ctg gag agc tcc gtg ccc agc ccc gtc cct gcc atc act gtg aac cag ggc
leu asp glu leu glu ser ser val pro ser pro val pro ala ile thr val asn gln gly
```

```
721/241                                 751/251
gag atg agc agc ccg cag cgc gtc acc tcc acc caa cag cag aca cgc atc tcg gcc tcc
glu met ser ser pro gln arg val thr ser thr gln gln gln thr arg ile ser ala ser
781/261                                 811/271                         γ - SPECIFIC SEQUENCE
tct gcc acc agg gag ctg gac gag ctg atg gct tcg ctg tcg gat ttc aag|ggc tcc tgg
ser ala thr arg glu leu asp glu leu met ala ser leu ser asp phe lys|gly ser trp
841/281                                 871/291
ccc ctg gag gag gtt gta ctt ctt gtc tcc atc agc tca tct gtc cag gag gga gaa aag
pro leu glu glu val val leu leu val ser ile ser ser ser val gln glu gly glu lys
901/301                                 931/311
tac ccc cat ccc tgt gct gcc aga cac cgt acc ccg agc ctc agg agt cct gac cag ccc
tyr pro his pro cys ala ala arg his arg thr pro ser leu arg ser pro asp gln pro
961/321                                 991/331
cct ccg tgt cca cag|ttc atg gcc cag ggg aag aca ggg agc agc tca ccc cct ggg ggg
pro pro cys pro gln|phe met ala gln gly lys thr gly ser ser ser pro pro gly gly
1021/341                                1051/351
ccc ccg aag ccc ggg agc cag ctg gac agc atg ctg ggg agc ctg cag tct gac ctg aac
pro pro lys pro gly ser gln leu asp ser met leu gly ser leu gln ser asp leu asn
1081/361                                1111/371
```

```
1141/381                                1171/391
aag ctg ggg gtc gcc aca gtc gcc aaa gga gtc tgc ggg gcc tgc aag aag ccc atc gcc
lys leu gly val ala thr val ala lys gly val cys gly ala cys lys lys pro ile ala
1201/401                                1231/411
ggg cag gtt gtg acc gcc atg ggg aag acg tgg cac ccc gag cac ttc gtc tgc acc cac
gly gln val val thr ala met gly lys thr trp his pro glu his phe val cys thr his
1261/421                                1291/431
tgc cag gag gag atc gga tcc cgg aac ttc ttc gag cgg gat gga cag ccc tac tgt gaa
cys gln glu glu ile gly ser arg asn phe phe glu arg asp gly gln pro tyr cys glu
1321/441                                1351/451
aag gac tac cac aac ctc ttc tcc ccg cgc tgc tac tac tgc aac ggc ccc atc ctg gat
lys asp tyr his asn leu phe ser pro arg cys tyr tyr cys asn gly pro ile leu asp
aaa gtg gtg aca gcc ctt gac cgg acg tgg cac cct gaa cac ttc ttc tgt gca cag tgt
lys val val thr ala leu asp arg thr trp his pro glu his phe phe cys ala gln cys

1381/461                                1411/471
gga gcc ttc ttt ggt ccc gaa ggg ttc cac gag aag gac ggc aag gcc tac tgt cgc aag
gly ala phe phe gly pro glu gly phe his glu lys asp gly lys ala tyr cys arg lys
1441/481                                1471/491
gac tac ttc gac atg ttc gca ccc aag tgt ggc ggc tgc gcc cgg gcc atc ctg gag aac
asp tyr phe asp met phe ala pro lys cys gly gly cys ala arg ala ile leu glu asn
```

```
1501/501                                1531/511
tat atc tca gcc ctc aac acg ctg tgg cat cct gag tgc ttt gtg tgc cgg gaa tgc ttc
tyr ile ser ala leu asn thr leu trp his pro glu cys phe val cys arg glu cys phe
1561/521                                1591/531
acg cca ttc gtg aac ggc agc ttc ttc gag cac gac ggg cag ccc tac tgt gag gtg cac
thr pro phe val asn gly ser phe phe glu his asp gly gln pro tyr cys glu val his
1621/541                                1651/551
tac cac gag cgg cgc ggc tcg ctg tgt tct ggc tgc cag aag ccc atc acc ggc cgc tgc
tyr his glu arg arg gly ser leu cys ser gly cys gln lys pro ile thr gly arg cys
1681/561                                1711/571
atc acc gcc atg gcc aag aag ttc cac ccc gag cac ttc gtc tgt gcc ttc tgc ctc aag
ile thr ala met ala lys lys phe his pro glu his phe val cys ala phe cys leu lys
1741/581                                1771/591
cag ctc aac aag ggc acc ttc aag gag cag aac gac aag cct tac tgt cag aac tgc ttc
gln leu asn lys gly thr phe lys glu gln asn asp lys pro tyr cys gln asn cys phe
1801/601
ctc aag ctc ttc tgc tag
leu lys leu phe cys AMB
```

```
1/1                                     31/11
atg gac gac ctc gac gcc ctg ctg gcg gac ttg gag tct acc acc tcc cac atc tcc aaa
Met asp asp leu asp ala leu leu ala asp leu glu ser thr thr ser his ile ser lys
61/21                                   91/31
cgg cct gtg ttc ttg tcg gag gag acc ccc tac tca tac cca act gga aac cac aca tac
arg pro val phe leu ser glu glu thr pro tyr ser tyr pro thr gly asn his thr tyr
121/41                                  151/51
cag gag att gcc gtg cca ccc ccc gtc ccc cca ccc ccg tcc agc gag gcc ctc aat ggc
gln glu ile ala val pro pro pro val pro pro pro pro ser ser glu ala leu asn gly
181/61                                  211/71
aca atc ctt gac ccc tta gac cag tgg cag ccc agc ggc tcc cga ttc atc cac cag cag
thr ile leu asp pro leu asp gln trp gln pro ser gly ser arg phe ile his gln gln
241/81                                  271/91
cct cag tcc tca tca cct gtg tac ggc tcc agt gcc aaa act tcc agt gtc tcc aac cct
pro gln ser ser ser pro val tyr gly ser ser ala lys thr ser ser val ser asn pro
301/101                                 331/111
cag gac agt gtt ggc tct ccg tgc tcc cga gtg ggt gag gag gag cac gtc tac agc ttc
gln asp ser val gly ser pro cys ser arg val gly glu glu glu his val tyr ser phe
```

FIG. 5B

361/121 391/131
ccc aac aag cag aaa tca gct gag cct tca ccc acc gta atg agc acg tcc ctg ggc agc
pro asn lys gln lys ser ala glu pro ser pro thr val met ser thr ser leu gly ser
421/141 451/151
aac ctt tct gaa ctc gac cgc ctg ctg ctg gaa ctg aac gct gta cag cat aac ccg cca
asn leu ser glu leu asp arg leu leu leu glu leu asn ala val gln his asn pro pro
481/161 511/171
ggc ttc cct gca gat gag gcc aac tca agc ccc ccg ctt cct ggg gcc ctg agc ccc ctc
gly phe pro ala asp glu ala asn ser ser pro pro leu pro gly ala leu ser pro leu
541/181 571/191
tat ggt gtc cca gag act aac agc ccc ttg gga ggc aaa gct ggg ccc ctg acg aaa gag
tyr gly val pro glu thr asn ser pro leu gly gly lys ala gly pro leu thr lys glu
601/201 631/211
aag cct aag cgg aat ggg ggc cgg ggc ctg gag gac gtg cgg ccc agt gtg gag agt ctc
lys pro lys arg asn gly gly arg gly leu glu asp val arg pro ser val glu ser leu
661/221 691/231
ttg gat gaa ctg gag agc tcc gtg ccc agc ccc gtc cct gcc atc act gtg aac cag ggc
leu asp glu leu glu ser ser val pro ser pro val pro ala ile thr val asn gln gly

```
721/241                                 751/251
gag atg agc agc ccg cag cgc gtc acc tcc acc caa cag cag aca cgc atc tcg gcc tcc
glu met ser ser pro gln arg val thr ser thr gln gln gln thr arg ile ser ala ser
781/261                                 811/271
tct gcc acc agg gag ctg gac gag ctg atg gct tcg ctg tcg gat ttc aag||ttc atg gcc
ser ala thr arg glu leu asp glu leu met ala ser leu ser asp phe lys||phe met ala
841/281                                 871/291
cag ggg aag aca ggg agc agc tca ccc cct ggg ggg ccc ccg aag ccc ggg agc cag ctg
gln gly lys thr gly ser ser ser pro pro gly gly pro pro lys pro gly ser gln leu
901/301                                 931/311
gac agc atg ctg ggg agc ctg cag tct gac ctg aac aag ctg ggg gtc gcc aca gtc gcc
asp ser met leu gly ser leu gln ser asp leu asn lys leu gly val ala thr val ala
961/321                                 991/331
aaa gga gtc tgc ggg gcc tgc aag aag ccc atc gcc ggg cag gtt gtg acc gcc atg ggg
lys gly val cys gly ala cys lys lys pro ile ala gly gln val val thr ala met gly
1021/341                                1051/351
aag acg tgg cac ccc gag cac ttc gtc tgc acc cac tgc cag gag gag atc gga tcc cgg
lys thr trp his pro glu his phe val cys thr his cys gln glu glu ile gly ser arg
1081/361                                1111/371
```

```
aac ttc ttc gag cgg gat gga cag ccc tac tgt gaa aag gac tac cac aac ctc ttc tcc
asn phe phe glu arg asp gly gln pro tyr cys glu lys asp tyr his asn leu phe ser
1141/381                                1171/391
ccg cgc tgc tac tac tgc aac ggc ccc atc ctg gat aaa gtg gtg aca gcc ctt gac cgg
pro arg cys tyr tyr cys asn gly pro ile leu asp lys val val thr ala leu asp arg
1201/401                                1231/411
acg tgg cac cct gaa cac ttc ttc tgt gca cag tgt gga gcc ttc ttt ggt ccc gaa ggg
thr trp his pro glu his phe phe cys ala gln cys gly ala phe phe gly pro glu gly
1261/421                                1291/431
ttc cac gag aag gac ggc aag gcc tac tgt cgc aag gac tac ttc gac atg ttc gca ccc
phe his glu lys asp gly lys ala tyr cys arg lys asp tyr phe asp met phe ala pro
1321/441                                1351/451
aag tgt ggc ggc tgc gcc cgg gcc atc ctg gag aac tat atc tca gcc ctc aac acg ctg
lys cys gly gly cys ala arg ala ile leu glu asn tyr ile ser ala leu asn thr leu
```

FIG.6B

```
1381/461                                1411/471
tgg cat cct gag tgc ttt gtg tgc cgg gaa tgc ttc acg cca ttc gtg aac ggc agc ttc
trp his pro glu cys phe val cys arg glu cys phe thr pro phe val asn gly ser phe
1441/481                                1471/491
ttc gag cac gac ggg cag ccc tac tgt gag gtg cac tac cac gag cgg cgc ggc tcg ctg
phe glu his asp gly gln pro tyr cys glu val his tyr his glu arg arg gly ser leu
1501/501                                1531/511
tgt tct ggc tgc cag aag ccc atc acc ggc cgc tgc atc acc gcc atg gcc aag aag ttc
cys ser gly cys gln lys pro ile thr gly arg cys ile thr ala met ala lys lys phe
1561/521                                1591/531
cac ccc gag cac ttc gtc tgt gcc ttc tgc ctc aag cag ctc aac aag ggc acc ttc aag
his pro glu his phe val cys ala phe cys leu lys gln leu asn lys gly thr phe lys
1621/541                                1651/551
gag cag aac gac aag cct tac tgt cag aac tgc ttc ctc aag ctc ttc tgc tag
glu gln asn asp lys pro tyr cys gln asn cys phe leu lys leu phe cys AMB
```

cttggcatctcagtgtttgggtgccttgcc cctgagccagggacactgtcatgccctggc cttgctgtgatgccaggagatggggaggga gggccgggtcagcctgcctgaggattgcag gtcctgcgtgtcgtgctctccctgggcttg gccatgcctgctgggtgccctcagcctttc cgaccctggtgggcccctccgaccaccagg

γ agtcctgctgacgtcactcccactttagGG

G

CTCCTGGCCCCTGGAGGAGGTTGTACTTCT

S W P L E E V V L L

TGTCTCCATCAGCTCATCTGTCCAGGAGGG

V S I S S S V Q E G

AGAAAAGTACCCCCATCCCTGTGCTGCCAG

E K Y P H P C A A R

ACACCGTACCCCGAGCCTCAGGAGTCCTGA

H R T P S L R S P D

CCAGCCCCCTCCGTGTCTACAGTTCATGGC

Q P P P C P Q F M A $Phe^{278}$ of α

FIG.7B-2

α PAXILLIN BLOT

FIG.9B
HeLa
NO LYSATE
U937
TOTAL
GST
GST-PAX α
GST-PAX β
GST-PAX γ
kDa
97.4–
αVINCULIN
1 2 3 4 5 6 7 8 9 10 11 12 13 14

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
( A ) LENGTH: 591 amino acids
( B ) TYPE: amino acid
( D ) TOPOLOGY: linear ( i i ) MOLECULE TYPE: protein ( v i ) ORIGINAL SOURCE:
( A ) ORGANISM: Homo sapiens
( G ) CELL TYPE: Monoblastic cell and placenta
( H ) CELL LINE: U937

( x i ) SEQUENCE DESCRIPTION: SEQ ID NO: 1:

Met Asp Asp Leu Asp Ala Leu Leu Ala Asp Leu Glu Ser Thr Thr Ser
1 5 10 15

His Ile Ser Lys Arg Pro Val Phe Leu Ser Glu Glu Thr Pro Tyr Ser
20 25 30

Tyr Pro Thr Gly Asn His Thr Tyr Gln Glu Ile Ala Val Pro Pro Pro
35 40 45

Val Pro Pro Pro Pro Ser Ser Glu Ala Leu Asn Gly Thr Ile Leu Asp
50 55 60

Pro Leu Asp Gln Trp Gln Pro Ser Gly Ser Arg Phe Ile His Gln Gln
65 70 75 80

Pro Gln Ser Ser Ser Pro Val Tyr Gly Ser Ser Ala Lys Thr Ser Ser
85 90 95

Val Ser Asn Pro Gln Asp Ser Val Gly Ser Pro Cys Ser Arg Val Gly
100 105 110

Glu Glu Glu His Val Tyr Ser Phe Pro Asn Lys Gln Lys Ser Ala Glu
115 120 125

Pro Ser Pro Thr Val Met Ser Thr Ser Leu Gly Ser Asn Leu Ser Glu
130 135 140

Leu Asp Arg Leu Leu Leu Glu Leu Asn Ala Val Gln His Asn Pro Pro
145 150 155 160

Gly Phe Pro Ala Asp Glu Ala Asn Ser Ser Pro Pro Leu Pro Gly Ala
165 170 175

Leu Ser Pro Leu Tyr Gly Val Pro Glu Thr Asn Ser Pro Leu Gly Gly
180 185 190

Lys Ala Gly Pro Leu Thr Lys Glu Lys Pro Lys Arg Asn Gly Gly Arg
195 200 205

Gly Leu Glu Asp Val Arg Pro Ser Val Glu Ser Leu Leu Asp Glu Leu
210 215 220

Glu Ser Ser Val Pro Ser Pro Val Pro Ala Ile Thr Val Asn Gln Gly
225 230 235 240

Glu Met Ser Ser Pro Gln Arg Val Thr Ser Thr Gln Gln Gln Thr Arg
245 250 255

Ile Ser Ala Ser Ser Ala Thr Arg Glu Leu Asp Glu Leu Met Ala Ser
260 265 270

Leu Ser Asp Phe Lys Ile Gln Asp Leu Glu Gln Arg Ala Asp Gly Glu
275 280 285

Arg Cys Trp Ala Ala Gly Trp Pro Arg Asp Gly Gly Arg Ser Ser Pro
290 295 300

Gly Gly Gln Asp Glu Gly Gly Phe Met Ala Gln Gly Lys Thr Gly Ser
305 310 315 320

Ser Ser Pro Pro Gly Gly Pro Pro Lys Pro Gly Ser Gln Leu Asp Ser
325 330 335

Met Leu Gly Ser Leu Gln Ser Asp Leu Asn Lys Leu Gly Val Ala Thr
340 345 350

-continued

```
Val Ala Lys Gly Val Cys Gly Ala Cys Lys Lys Pro Ile Ala Gly Gln
        355                 360                 365

Val Val Thr Ala Met Gly Lys Thr Trp His Pro Glu His Phe Val Cys
    370                 375                 380

Thr His Cys Gln Glu Glu Ile Gly Ser Arg Asn Phe Phe Glu Arg Asp
385                 390                 395                 400

Gly Gln Pro Tyr Cys Glu Lys Asp Tyr His Asn Leu Phe Ser Pro Arg
                405                 410                 415

Cys Tyr Tyr Cys Asn Gly Pro Ile Leu Asp Lys Val Val Thr Ala Leu
            420                 425                 430

Asp Arg Thr Trp His Pro Glu His Phe Phe Cys Ala Gln Cys Gly Ala
        435                 440                 445

Phe Phe Gly Pro Glu Gly Phe His Glu Lys Asp Gly Lys Ala Tyr Cys
    450                 455                 460

Arg Lys Asp Tyr Phe Asp Met Phe Ala Pro Lys Cys Gly Gly Cys Ala
465                 470                 475                 480

Arg Ala Ile Leu Glu Asn Tyr Ile Ser Ala Leu Asn Thr Leu Trp His
                485                 490                 495

Pro Glu Cys Phe Val Cys Arg Glu Cys Phe Thr Pro Phe Val Asn Gly
            500                 505                 510

Ser Phe Phe Glu His Asp Gly Gln Pro Tyr Cys Glu Val His Tyr His
        515                 520                 525

Glu Arg Arg Gly Ser Leu Cys Ser Gly Cys Gln Lys Pro Ile Thr Gly
    530                 535                 540

Arg Cys Ile Thr Ala Met Ala Lys Lys Phe His Pro Glu His Phe Val
545                 550                 555                 560

Cys Ala Phe Cys Leu Lys Gln Leu Asn Lys Gly Thr Phe Lys Glu Gln
                565                 570                 575

Asn Asp Lys Pro Tyr Cys Gln Asn Cys Phe Leu Lys Leu Phe Cys
            580                 585                 590
```

( 2 ) INFORMATION FOR SEQ ID NO: 2:

( i ) SEQUENCE CHARACTERISTICS:
( A ) LENGTH: 605 amino acids
( B ) TYPE: amino acid
( D ) TOPOLOGY: linear ( i i ) MOLECULE TYPE: protein ( v i ) ORIGINAL SOURCE:
( A ) ORGANISM: Homo sapiens
( G ) CELL TYPE: Monoblastic cell and placenta
( H ) CELL LINE: U937

( x i ) SEQUENCE DESCRIPTION: SEQ ID NO: 2:

```
Met Asp Asp Leu Asp Ala Leu Leu Ala Asp Leu Glu Ser Thr Thr Ser
  1               5                  10                  15

His Ile Ser Lys Arg Pro Val Phe Leu Ser Glu Glu Thr Pro Tyr Ser
             20                  25                  30

Tyr Pro Thr Gly Asn His Thr Tyr Gln Glu Ile Ala Val Pro Pro Pro
         35                  40                  45

Val Pro Pro Pro Pro Ser Ser Glu Ala Leu Asn Gly Thr Ile Leu Asp
     50                  55                  60

Pro Leu Asp Gln Trp Gln Pro Ser Gly Ser Arg Phe Ile His Gln Gln
 65                  70                  75                  80

Pro Gln Ser Ser Ser Pro Val Tyr Gly Ser Ser Ala Lys Thr Ser Ser
                 85                  90                  95
```

-continued

| | | | | | | | | | | | | | | | |
|---|---|---|---|---|---|---|---|---|---|---|---|---|---|---|---|
| Val | Ser | Asn | Pro | Gln | Asp | Ser | Val | Gly | Ser | Pro | Cys | Ser | Arg | Val | Gly |
| | | | 100 | | | | | 105 | | | | | 110 | | |
| Glu | Glu | Glu | His | Val | Tyr | Ser | Phe | Pro | Asn | Lys | Gln | Lys | Ser | Ala | Glu |
| | | 115 | | | | | 120 | | | | | 125 | | | |
| Pro | Ser | Pro | Thr | Val | Met | Ser | Thr | Ser | Leu | Gly | Ser | Asn | Leu | Ser | Glu |
| | 130 | | | | | 135 | | | | | 140 | | | | |
| Leu | Asp | Arg | Leu | Leu | Leu | Glu | Leu | Asn | Ala | Val | Gln | His | Asn | Pro | Pro |
| 145 | | | | | 150 | | | | | 155 | | | | | 160 |
| Gly | Phe | Pro | Ala | Asp | Glu | Ala | Asn | Ser | Ser | Pro | Pro | Leu | Pro | Gly | Ala |
| | | | | 165 | | | | | 170 | | | | | 175 | |
| Leu | Ser | Pro | Leu | Tyr | Gly | Val | Pro | Glu | Thr | Asn | Ser | Pro | Leu | Gly | Gly |
| | | | 180 | | | | | 185 | | | | | 190 | | |
| Lys | Ala | Gly | Pro | Leu | Thr | Lys | Glu | Lys | Pro | Lys | Arg | Asn | Gly | Gly | Arg |
| | | 195 | | | | | 200 | | | | | 205 | | | |
| Gly | Leu | Glu | Asp | Val | Arg | Pro | Ser | Val | Glu | Ser | Leu | Leu | Asp | Glu | Leu |
| | 210 | | | | | 215 | | | | | 220 | | | | |
| Glu | Ser | Ser | Val | Pro | Ser | Pro | Val | Pro | Ala | Ile | Thr | Val | Asn | Gln | Gly |
| 225 | | | | | 230 | | | | | 235 | | | | | 240 |
| Glu | Met | Ser | Ser | Pro | Gln | Arg | Val | Thr | Ser | Thr | Gln | Gln | Gln | Thr | Arg |
| | | | | 245 | | | | | 250 | | | | | 255 | |
| Ile | Ser | Ala | Ser | Ser | Ala | Thr | Arg | Glu | Leu | Asp | Glu | Leu | Met | Ala | Ser |
| | | | 260 | | | | | 265 | | | | | 270 | | |
| Leu | Ser | Asp | Phe | Lys | Gly | Ser | Trp | Pro | Leu | Glu | Glu | Val | Val | Leu | Leu |
| | | 275 | | | | | 280 | | | | | 285 | | | |
| Val | Ser | Ile | Ser | Ser | Ser | Val | Gln | Glu | Gly | Glu | Lys | Tyr | Pro | His | Pro |
| | 290 | | | | | 295 | | | | | 300 | | | | |
| Cys | Ala | Ala | Arg | His | Arg | Thr | Pro | Ser | Leu | Arg | Ser | Pro | Asp | Gln | Pro |
| 305 | | | | | 310 | | | | | 315 | | | | | 320 |
| Pro | Pro | Cys | Pro | Gln | Phe | Met | Ala | Gln | Gly | Lys | Thr | Gly | Ser | Ser | Ser |
| | | | | 325 | | | | | 330 | | | | | 335 | |
| Pro | Pro | Gly | Gly | Pro | Pro | Lys | Pro | Gly | Ser | Gln | Leu | Asp | Ser | Met | Leu |
| | | | 340 | | | | | 345 | | | | | 350 | | |
| Gly | Ser | Leu | Gln | Ser | Asp | Leu | Asn | Lys | Leu | Gly | Val | Ala | Thr | Val | Ala |
| | | 355 | | | | | 360 | | | | | 365 | | | |
| Lys | Gly | Val | Cys | Gly | Ala | Cys | Lys | Lys | Pro | Ile | Ala | Gly | Gln | Val | Val |
| | 370 | | | | | 375 | | | | | 380 | | | | |
| Thr | Ala | Met | Gly | Lys | Thr | Trp | His | Pro | Glu | His | Phe | Val | Cys | Thr | His |
| 385 | | | | | 390 | | | | | 395 | | | | | 400 |
| Cys | Gln | Glu | Glu | Ile | Gly | Ser | Arg | Asn | Phe | Phe | Glu | Arg | Asp | Gly | Gln |
| | | | | 405 | | | | | 410 | | | | | 415 | |
| Pro | Tyr | Cys | Glu | Lys | Asp | Tyr | His | Asn | Leu | Phe | Ser | Pro | Arg | Cys | Tyr |
| | | | 420 | | | | | 425 | | | | | 430 | | |
| Tyr | Cys | Asn | Gly | Pro | Ile | Leu | Asp | Lys | Val | Val | Thr | Ala | Leu | Asp | Arg |
| | | 435 | | | | | 440 | | | | | 445 | | | |
| Thr | Trp | His | Pro | Glu | His | Phe | Phe | Cys | Ala | Gln | Cys | Gly | Ala | Phe | Phe |
| | 450 | | | | | 455 | | | | | 460 | | | | |
| Gly | Pro | Glu | Gly | Phe | His | Glu | Lys | Asp | Gly | Lys | Ala | Tyr | Cys | Arg | Lys |
| 465 | | | | | 470 | | | | | 475 | | | | | 480 |
| Asp | Tyr | Phe | Asp | Met | Phe | Ala | Pro | Lys | Cys | Gly | Gly | Cys | Ala | Arg | Ala |
| | | | | 485 | | | | | 490 | | | | | 495 | |
| Ile | Leu | Glu | Asn | Tyr | Ile | Ser | Ala | Leu | Asn | Thr | Leu | Trp | His | Pro | Glu |
| | | | 500 | | | | | 505 | | | | | 510 | | |
| Cys | Phe | Val | Cys | Arg | Glu | Cys | Phe | Thr | Pro | Phe | Val | Asn | Gly | Ser | Phe |

-continued 515 520 525

Phe Glu His Asp Gly Gln Pro Tyr Cys Glu Val His Tyr His Glu Arg
530 535 540

Arg Gly Ser Leu Cys Ser Gly Cys Gln Lys Pro Ile Thr Gly Arg Cys
545 550 555 560

Ile Thr Ala Met Ala Lys Lys Phe His Pro Glu His Phe Val Cys Ala
565 570 575

Phe Cys Leu Lys Gln Leu Asn Lys Gly Thr Phe Lys Glu Gln Asn Asp
580 585 590

Lys Pro Tyr Cys Gln Asn Cys Phe Leu Lys Leu Phe Cys
595 600 605

( 2 ) INFORMATION FOR SEQ ID NO: 3:

( i ) SEQUENCE CHARACTERISTICS:
( A ) LENGTH: 1776 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO: 3:

ATGGACGACC TCGACGCCCT GCTGGCGGAC TTGGAGTCTA CCACCTCCCA CATCTCCAAA 60

CGGCCTGTGT TCTTGTCGGA GGAGACCCCC TACTCATACC CAACTGGAAA CCACACATAC 120

CAGGAGATTG CCGTGCCACC CCCCGTCCCC CCACCCCCGT CCAGCGAGGC CCTCAATGGC 180

ACAATCCTTG ACCCCTTAGA CCAGTGGCAG CCCAGCGGCT CCCGATTCAT CCACCAGCAG 240

CCTCAGTCCT CATCACCTGT GTACGGCTCC AGTGCCAAAA CTTCCAGTGT CTCCAACCCT 300

CAGGACAGTG TTGGCTCTCC GTGCTCCCGA GTGGGTGAGG AGGAGCACGT CTACAGCTTC 360

CCCAACAAGC AGAAATCAGC TGAGCCTTCA CCCACCGTAA TGAGCACGTC CCTGGGCAGC 420

AACCTTTCTG AACTCGACCG CCTGCTGCTG GAACTGAACG CTGTACAGCA TAACCCGCCA 480

GGCTTCCCTG CAGATGAGGC CAACTCAAGC CCCCCGCTTC CTGGGGCCCT GAGCCCCCTC 540

TATGGTGTCC CAGAGACTAA CAGCCCCTTG GGAGGCAAAG CTGGGCCCCT GACGAAAGAG 600

AAGCCTAAGC GGAATGGGGG CCGGGGCCTG GAGGACGTGC GGCCCAGTGT GGAGAGTCTC 660

TTGGATGAAC TGGAGAGCTC CGTGCCCAGC CCCGTCCCTG CCATCACTGT GAACCAGGGC 720

GAGATGAGCA GCCCGCAGCG CGTCACCTCC ACCCAACAGC AGACACGCAT CTCGGCCTCC 780

TCTGCCACCA GGGAGCTGGA CGAGCTGATG GCTTCGCTGT CGGATTTCAA GATCCAGGAC 840

CTGGAGCAAA GAGCGGATGG GGAGCGGTGC TGGGCGGCCG GCTGGCCTCG GGACGGCGGG 900

CGGAGCAGCC CCGGAGGGCA GGACGAGGGA GGGTTCATGG CCCAGGGGAA GACAGGGAGC 960

AGCTCACCCC CTGGGGGGCC CCCGAAGCCC GGGAGCCAGC TGGACAGCAT GCTGGGGAGC 1020

CTGCAGTCTG ACCTGAACAA GCTGGGGGTC GCCACAGTCG CCAAAGGAGT CTGCGGGGCC 1080

TGCAAGAAGC CCATCGCCGG GCAGGTTGTG ACCGCCATGG GGAAGACGTG GCACCCCGAG 1140

CACTTCGTCT GCACCCACTG CCAGGAGGAG ATCGGATCCC GGAACTTCTT CGAGCGGGAT 1200

GGACAGCCCT ACTGTGAAAA GGACTACCAC AACCTCTTCT CCCCGCGCTG CTACTACTGC 1260

AACGGCCCCA TCCTGGATAA AGTGGTGACA GCCCTTGACC GGACGTGGCA CCCTGAACAC 1320

TTCTTCTGTG CACAGTGTGG AGCCTTCTTT GGTCCCGAAG GGTTCCACGA GAAGGACGGC 1380

AAGGCCTACT GTCGCAAGGA CTACTTCGAC ATGTTCGCAC CCAAGTGTGG CGGCTGCGCC 1440

CGGGCCATCC TGGAGAACTA TATCTCAGCC CTCAACACGC TGTGGCATCC TGAGTGCTTT 1500

-continued

| | | | | | | |
|---|---|---|---|---|---|---|
| GTGTGCCGGG | AATGCTTCAC | GCCATTCGTG | AACGGCAGCT | TCTTCGAGCA | CGACGGGCAG | 1560 |
| CCCTACTGTG | AGGTGCACTA | CCACGAGCGG | CGCGGCTCGC | TGTGTTCTGG | CTGCCAGAAG | 1620 |
| CCCATCACCG | GCCGCTGCAT | CACCGCCATG | GCCAAGAAGT | TCCACCCCGA | GCACTTCGTC | 1680 |
| TGTGCCTTCT | GCCTCAAGCA | GCTCAACAAG | GGCACCTTCA | AGGAGCAGAA | CGACAAGCCT | 1740 |
| TACTGTCAGA | ACTGCTTCCT | CAAGCTCTTC | TGCTAG | | | 1776 |

( 2 ) INFORMATION FOR SEQ ID NO: 4:

( i ) SEQUENCE CHARACTERISTICS:
( A ) LENGTH: 1818 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO: 4:

| | | | | | | |
|---|---|---|---|---|---|---|
| ATGGACGACC | TCGACGCCCT | GCTGGCGGAC | TTGGAGTCTA | CCACCTCCCA | CATCTCCAAA | 60 |
| CGGCCTGTGT | TCTTGTCGGA | GGAGACCCCC | TACTCATACC | CAACTGGAAA | CCACACATAC | 120 |
| CAGGAGATTG | CCGTGCCACC | CCCCGTCCCC | CCACCCCCGT | CCAGCGAGGC | CCTCAATGGC | 180 |
| ACAATCCTTG | ACCCCTTAGA | CCAGTGGCAG | CCCAGCGGCT | CCCGATTCAT | CCACCAGCAG | 240 |
| CCTCAGTCCT | CATCACCTGT | GTACGGCTCC | AGTGCCAAAA | CTTCCAGTGT | CTCCAACCCT | 300 |
| CAGGACAGTG | TTGGCTCTCC | GTGCTCCCGA | GTGGGTGAGG | AGGAGCACGT | CTACAGCTTC | 360 |
| CCCAACAAGC | AGAAATCAGC | TGAGCCTTCA | CCCACCGTAA | TGAGCACGTC | CCTGGGCAGC | 420 |
| AACCTTTCTG | AACTCGACCG | CCTGCTGCTG | GAACTGAACG | CTGTACAGCA | TAACCCGCCA | 480 |
| GGCTTCCCTG | CAGATGAGGC | CAACTCAAGC | CCCCCGCTTC | CTGGGGCCCT | GAGCCCCCTC | 540 |
| TATGGTGTCC | CAGAGACTAA | CAGCCCCTTG | GGAGGCAAAG | CTGGGCCCCT | GACGAAAGAG | 600 |
| AAGCCTAAGC | GGAATGGGGG | CCGGGGCCTG | GAGGACGTGC | GGCCCAGTGT | GGAGAGTCTC | 660 |
| TTGGATGAAC | TGGAGAGCTC | CGTGCCCAGC | CCCGTCCCTG | CCATCACTGT | GAACCAGGGC | 720 |
| GAGATGAGCA | GCCCGCAGCG | CGTCACCTCC | ACCCAACAGC | AGACACGCAT | CTCGGCCTCC | 780 |
| TCTGCCACCA | GGGAGCTGGA | CGAGCTGATG | GCTTCGCTGT | CGGATTTCAA | GGGCTCCTGG | 840 |
| CCCCTGGAGG | AGGTTGTACT | TCTTGTCTCC | ATCAGCTCAT | CTGTCCAGGA | GGGAGAAAAG | 900 |
| TACCCCCATC | CCTGTGCTGC | CAGACACCGT | ACCCCGAGCC | TCAGGAGTCC | TGACCAGCCC | 960 |
| CCTCCGTGTC | CACAGTTCAT | GGCCCAGGGG | AAGACAGGGA | GCAGCTCACC | CCCTGGGGGG | 1020 |
| CCCCCGAAGC | CCGGGAGCCA | GCTGGACAGC | ATGCTGGGGA | GCCTGCAGTC | TGACCTGAAC | 1080 |
| AAGCTGGGGG | TCGCCACAGT | CGCCAAAGGA | GTCTGCGGGG | CCTGCAAGAA | GCCCATCGCC | 1140 |
| GGGCAGGTTG | TGACCGCCAT | GGGGAAGACG | TGGCACCCCG | AGCACTTCGT | CTGCACCCAC | 1200 |
| TGCCAGGAGG | AGATCGGATC | CCGGAACTTC | TTCGAGCGGG | ATGGACAGCC | CTACTGTGAA | 1260 |
| AAGGACTACC | ACAACCTCTT | CTCCCCGCGC | TGCTACTACT | GCAACGGCCC | CATCCTGGAT | 1320 |
| AAAGTGGTGA | CAGCCCTTGA | CCGGACGTGG | CACCCTGAAC | ACTTCTTCTG | TGCACAGTGT | 1380 |
| GGAGCCTTCT | TTGGTCCCGA | AGGGTTCCAC | GAGAAGGACG | GCAAGGCCTA | CTGTCGCAAG | 1440 |
| GACTACTTCG | ACATGTTCGC | ACCCAAGTGT | GGCGGCTGCG | CCCGGGCCAT | CCTGGAGAAC | 1500 |
| TATATCTCAG | CCCTCAACAC | GCTGTGGCAT | CCTGAGTGCT | TTGTGTGCCG | GGAATGCTTC | 1560 |
| ACGCCATTCG | TGAACGGCAG | CTTCTTCGAG | CACGACGGGC | AGCCCTACTG | TGAGGTGCAC | 1620 |
| TACCACGAGC | GGCGCGGCTC | GCTGTGTTCT | GGCTGCCAGA | AGCCCATCAC | CGGCCGCTGC | 1680 |
| ATCACCGCCA | TGGCCAAGAA | GTTCCACCCC | GAGCACTTCG | TCTGTGCCTT | CTGCCTCAAG | 1740 |

-continued

```
CAGCTCAACA AGGGCACCTT CAAGGAGCAG AACGACAAGC CTTACTGTCA GAACTGCTTC    1800

CTCAAGCTCT TCTGCTAG                                                  1818
```

( 2 ) INFORMATION FOR SEQ ID NO: 5:

( i ) SEQUENCE CHARACTERISTICS:
( A ) LENGTH: 1776 base pairs
( B ) TYPE: nucleic acid
( C ) STRANDEDNESS: double
( D ) TOPOLOGY: linear ( i i ) MOLECULE TYPE: cDNA to mRNA ( i x ) FEATURE:
( A ) NAME/KEY: CDS
( B ) LOCATION:1..1773

( x i ) SEQUENCE DESCRIPTION: SEQ ID NO: 5:

```
ATG GAC GAC CTC GAC GCC CTG CTG GCG GAC TTG GAG TCT ACC ACC TCC    48
Met Asp Asp Leu Asp Ala Leu Leu Ala Asp Leu Glu Ser Thr Thr Ser
  1               5                  10                  15

CAC ATC TCC AAA CGG CCT GTG TTC TTG TCG GAG GAG ACC CCC TAC TCA    96
His Ile Ser Lys Arg Pro Val Phe Leu Ser Glu Glu Thr Pro Tyr Ser
             20                  25                  30

TAC CCA ACT GGA AAC CAC ACA TAC CAG GAG ATT GCC GTG CCA CCC CCC   144
Tyr Pro Thr Gly Asn His Thr Tyr Gln Glu Ile Ala Val Pro Pro Pro
         35                  40                  45

GTC CCC CCA CCC CCG TCC AGC GAG GCC CTC AAT GGC ACA ATC CTT GAC   192
Val Pro Pro Pro Pro Ser Ser Glu Ala Leu Asn Gly Thr Ile Leu Asp
     50                  55                  60

CCC TTA GAC CAG TGG CAG CCC AGC GGC TCC CGA TTC ATC CAC CAG CAG   240
Pro Leu Asp Gln Trp Gln Pro Ser Gly Ser Arg Phe Ile His Gln Gln
 65                  70                  75                  80

CCT CAG TCC TCA TCA CCT GTG TAC GGC TCC AGT GCC AAA ACT TCC AGT   288
Pro Gln Ser Ser Ser Pro Val Tyr Gly Ser Ser Ala Lys Thr Ser Ser
                 85                  90                  95

GTC TCC AAC CCT CAG GAC AGT GTT GGC TCT CCG TGC TCC CGA GTG GGT   336
Val Ser Asn Pro Gln Asp Ser Val Gly Ser Pro Cys Ser Arg Val Gly
            100                 105                 110

GAG GAG GAG CAC GTC TAC AGC TTC CCC AAC AAG CAG AAA TCA GCT GAG   384
Glu Glu Glu His Val Tyr Ser Phe Pro Asn Lys Gln Lys Ser Ala Glu
        115                 120                 125

CCT TCA CCC ACC GTA ATG AGC ACG TCC CTG GGC AGC AAC CTT TCT GAA   432
Pro Ser Pro Thr Val Met Ser Thr Ser Leu Gly Ser Asn Leu Ser Glu
    130                 135                 140

CTC GAC CGC CTG CTG CTG GAA CTG AAC GCT GTA CAG CAT AAC CCG CCA   480
Leu Asp Arg Leu Leu Leu Glu Leu Asn Ala Val Gln His Asn Pro Pro
145                 150                 155                 160

GGC TTC CCT GCA GAT GAG GCC AAC TCA AGC CCC CCG CTT CCT GGG GCC   528
Gly Phe Pro Ala Asp Glu Ala Asn Ser Ser Pro Pro Leu Pro Gly Ala
                165                 170                 175

CTG AGC CCC CTC TAT GGT GTC CCA GAG ACT AAC AGC CCC TTG GGA GGC   576
Leu Ser Pro Leu Tyr Gly Val Pro Glu Thr Asn Ser Pro Leu Gly Gly
            180                 185                 190

AAA GCT GGG CCC CTG ACG AAA GAG AAG CCT AAG CGG AAT GGG GGC CGG   624
Lys Ala Gly Pro Leu Thr Lys Glu Lys Pro Lys Arg Asn Gly Gly Arg
        195                 200                 205

GGC CTG GAG GAC GTG CGG CCC AGT GTG GAG AGT CTC TTG GAT GAA CTG   672
Gly Leu Glu Asp Val Arg Pro Ser Val Glu Ser Leu Leu Asp Glu Leu
    210                 215                 220

GAG AGC TCC GTG CCC AGC CCC GTC CCT GCC ATC ACT GTG AAC CAG GGC   720
Glu Ser Ser Val Pro Ser Pro Val Pro Ala Ile Thr Val Asn Gln Gly
```

-continued 225 230 235 240

GAG ATG AGC AGC CCG CAG CGC GTC ACC TCC ACC CAA CAG CAG ACA CGC 768
Glu Met Ser Ser Pro Gln Arg Val Thr Ser Thr Gln Gln Gln Thr Arg
245 250 255

ATC TCG GCC TCC TCT GCC ACC AGG GAG CTG GAC GAG CTG ATG GCT TCG 816
Ile Ser Ala Ser Ser Ala Thr Arg Glu Leu Asp Glu Leu Met Ala Ser
260 265 270

CTG TCG GAT TTC AAG ATC CAG GAC CTG GAG CAA AGA GCG GAT GGG GAG 864
Leu Ser Asp Phe Lys Ile Gln Asp Leu Glu Gln Arg Ala Asp Gly Glu
275 280 285

CGG TGC TGG GCG GCC GGC TGG CCT CGG GAC GGC GGG CGG AGC AGC CCC 912
Arg Cys Trp Ala Ala Gly Trp Pro Arg Asp Gly Gly Arg Ser Ser Pro
290 295 300

GGA GGG CAG GAC GAG GGA GGG TTC ATG GCC CAG GGG AAG ACA GGG AGC 960
Gly Gly Gln Asp Glu Gly Gly Phe Met Ala Gln Gly Lys Thr Gly Ser
305 310 315 320

AGC TCA CCC CCT GGG GGG CCC CCG AAG CCC GGG AGC CAG CTG GAC AGC 1008
Ser Ser Pro Pro Gly Gly Pro Pro Lys Pro Gly Ser Gln Leu Asp Ser
325 330 335

ATG CTG GGG AGC CTG CAG TCT GAC CTG AAC AAG CTG GGG GTC GCC ACA 1056
Met Leu Gly Ser Leu Gln Ser Asp Leu Asn Lys Leu Gly Val Ala Thr
340 345 350

GTC GCC AAA GGA GTC TGC GGG GCC TGC AAG AAG CCC ATC GCC GGG CAG 1104
Val Ala Lys Gly Val Cys Gly Ala Cys Lys Lys Pro Ile Ala Gly Gln
355 360 365

GTT GTG ACC GCC ATG GGG AAG ACG TGG CAC CCC GAG CAC TTC GTC TGC 1152
Val Val Thr Ala Met Gly Lys Thr Trp His Pro Glu His Phe Val Cys
370 375 380

ACC CAC TGC CAG GAG GAG ATC GGA TCC CGG AAC TTC TTC GAG CGG GAT 1200
Thr His Cys Gln Glu Glu Ile Gly Ser Arg Asn Phe Phe Glu Arg Asp
385 390 395 400

GGA CAG CCC TAC TGT GAA AAG GAC TAC CAC AAC CTC TTC TCC CCG CGC 1248
Gly Gln Pro Tyr Cys Glu Lys Asp Tyr His Asn Leu Phe Ser Pro Arg
405 410 415

TGC TAC TAC TGC AAC GGC CCC ATC CTG GAT AAA GTG GTG ACA GCC CTT 1296
Cys Tyr Tyr Cys Asn Gly Pro Ile Leu Asp Lys Val Val Thr Ala Leu
420 425 430

GAC CGG ACG TGG CAC CCT GAA CAC TTC TTC TGT GCA CAG TGT GGA GCC 1344
Asp Arg Thr Trp His Pro Glu His Phe Phe Cys Ala Gln Cys Gly Ala
435 440 445

TTC TTT GGT CCC GAA GGG TTC CAC GAG AAG GAC GGC AAG GCC TAC TGT 1392
Phe Phe Gly Pro Glu Gly Phe His Glu Lys Asp Gly Lys Ala Tyr Cys
450 455 460

CGC AAG GAC TAC TTC GAC ATG TTC GCA CCC AAG TGT GGC GGC TGC GCC 1440
Arg Lys Asp Tyr Phe Asp Met Phe Ala Pro Lys Cys Gly Gly Cys Ala
465 470 475 480

CGG GCC ATC CTG GAG AAC TAT ATC TCA GCC CTC AAC ACG CTG TGG CAT 1488
Arg Ala Ile Leu Glu Asn Tyr Ile Ser Ala Leu Asn Thr Leu Trp His
485 490 495

CCT GAG TGC TTT GTG TGC CGG GAA TGC TTC ACG CCA TTC GTG AAC GGC 1536
Pro Glu Cys Phe Val Cys Arg Glu Cys Phe Thr Pro Phe Val Asn Gly
500 505 510

AGC TTC TTC GAG CAC GAC GGG CAG CCC TAC TGT GAG GTG CAC TAC CAC 1584
Ser Phe Phe Glu His Asp Gly Gln Pro Tyr Cys Glu Val His Tyr His
515 520 525

GAG CGG CGC GGC TCG CTG TGT TCT GGC TGC CAG AAG CCC ATC ACC GGC 1632
Glu Arg Arg Gly Ser Leu Cys Ser Gly Cys Gln Lys Pro Ile Thr Gly
530 535 540

CGC TGC ATC ACC GCC ATG GCC AAG AAG TTC CAC CCC GAG CAC TTC GTC 1680
Arg Cys Ile Thr Ala Met Ala Lys Lys Phe His Pro Glu His Phe Val

-continued 545 550 555 560

TGT GCC TTC TGC CTC AAG CAG CTC AAC AAG GGC ACC TTC AAG GAG CAG 1728
Cys Ala Phe Cys Leu Lys Gln Leu Asn Lys Gly Thr Phe Lys Glu Gln
565 570 575

AAC GAC AAG CCT TAC TGT CAG AAC TGC TTC CTC AAG CTC TTC TGC 1773
Asn Asp Lys Pro Tyr Cys Gln Asn Cys Phe Leu Lys Leu Phe Cys
580 585 590

TAG 1776

( 2 ) INFORMATION FOR SEQ ID NO: 6:

( i ) SEQUENCE CHARACTERISTICS:
( A ) LENGTH: 1818 base pairs
( B ) TYPE: nucleic acid
( C ) STRANDEDNESS: double
( D ) TOPOLOGY: linear ( i i ) MOLECULE TYPE: cDNA to mRNA ( i x ) FEATURE:
( A ) NAME/KEY: CDS
( B ) LOCATION:1..1815

( x i ) SEQUENCE DESCRIPTION: SEQ ID NO: 6:

ATG GAC GAC CTC GAC GCC CTG CTG GCG GAC TTG GAG TCT ACC ACC TCC 48
Met Asp Asp Leu Asp Ala Leu Leu Ala Asp Leu Glu Ser Thr Thr Ser
1 5 10 15

CAC ATC TCC AAA CGG CCT GTG TTC TTG TCG GAG GAG ACC CCC TAC TCA 96
His Ile Ser Lys Arg Pro Val Phe Leu Ser Glu Glu Thr Pro Tyr Ser
20 25 30

TAC CCA ACT GGA AAC CAC ACA TAC CAG GAG ATT GCC GTG CCA CCC CCC 144
Tyr Pro Thr Gly Asn His Thr Tyr Gln Glu Ile Ala Val Pro Pro Pro
35 40 45

GTC CCC CCA CCC CCG TCC AGC GAG GCC CTC AAT GGC ACA ATC CTT GAC 192
Val Pro Pro Pro Pro Ser Ser Glu Ala Leu Asn Gly Thr Ile Leu Asp
50 55 60

CCC TTA GAC CAG TGG CAG CCC AGC GGC TCC CGA TTC ATC CAC CAG CAG 240
Pro Leu Asp Gln Trp Gln Pro Ser Gly Ser Arg Phe Ile His Gln Gln
65 70 75 80

CCT CAG TCC TCA TCA CCT GTG TAC GGC TCC AGT GCC AAA ACT TCC AGT 288
Pro Gln Ser Ser Ser Pro Val Tyr Gly Ser Ser Ala Lys Thr Ser Ser
85 90 95

GTC TCC AAC CCT CAG GAC AGT GTT GGC TCT CCG TGC TCC CGA GTG GGT 336
Val Ser Asn Pro Gln Asp Ser Val Gly Ser Pro Cys Ser Arg Val Gly
100 105 110

GAG GAG GAG CAC GTC TAC AGC TTC CCC AAC AAG CAG AAA TCA GCT GAG 384
Glu Glu Glu His Val Tyr Ser Phe Pro Asn Lys Gln Lys Ser Ala Glu
115 120 125

CCT TCA CCC ACC GTA ATG AGC ACG TCC CTG GGC AGC AAC CTT TCT GAA 432
Pro Ser Pro Thr Val Met Ser Thr Ser Leu Gly Ser Asn Leu Ser Glu
130 135 140

CTC GAC CGC CTG CTG CTG GAA CTG AAC GCT GTA CAG CAT AAC CCG CCA 480
Leu Asp Arg Leu Leu Leu Glu Leu Asn Ala Val Gln His Asn Pro Pro
145 150 155 160

GGC TTC CCT GCA GAT GAG GCC AAC TCA AGC CCC CCG CTT CCT GGG GCC 528
Gly Phe Pro Ala Asp Glu Ala Asn Ser Ser Pro Pro Leu Pro Gly Ala
165 170 175

CTG AGC CCC CTC TAT GGT GTC CCA GAG ACT AAC AGC CCC TTG GGA GGC 576
Leu Ser Pro Leu Tyr Gly Val Pro Glu Thr Asn Ser Pro Leu Gly Gly
180 185 190

AAA GCT GGG CCC CTG ACG AAA GAG AAG CCT AAG CGG AAT GGG GGC CGG 624
Lys Ala Gly Pro Leu Thr Lys Glu Lys Pro Lys Arg Asn Gly Gly Arg
195 200 205

-continued

GGC CTG GAG GAC GTG CGG CCC AGT GTG GAG AGT CTC TTG GAT GAA CTG 672
Gly Leu Glu Asp Val Arg Pro Ser Val Glu Ser Leu Leu Asp Glu Leu
210 215 220

GAG AGC TCC GTG CCC AGC CCC GTC CCT GCC ATC ACT GTG AAC CAG GGC 720
Glu Ser Ser Val Pro Ser Pro Val Pro Ala Ile Thr Val Asn Gln Gly
225 230 235 240

GAG ATG AGC AGC CCG CAG CGC GTC ACC TCC ACC CAA CAG CAG ACA CGC 768
Glu Met Ser Ser Pro Gln Arg Val Thr Ser Thr Gln Gln Gln Thr Arg
245 250 255

ATC TCG GCC TCC TCT GCC ACC AGG GAG CTG GAC GAG CTG ATG GCT TCG 816
Ile Ser Ala Ser Ser Ala Thr Arg Glu Leu Asp Glu Leu Met Ala Ser
260 265 270

CTG TCG GAT TTC AAG GGC TCC TGG CCC CTG GAG GAG GTT GTA CTT CTT 864
Leu Ser Asp Phe Lys Gly Ser Trp Pro Leu Glu Glu Val Val Leu Leu
275 280 285

GTC TCC ATC AGC TCA TCT GTC CAG GAG GGA GAA AAG TAC CCC CAT CCC 912
Val Ser Ile Ser Ser Ser Val Gln Glu Gly Glu Lys Tyr Pro His Pro
290 295 300

TGT GCT GCC AGA CAC CGT ACC CCG AGC CTC AGG AGT CCT GAC CAG CCC 960
Cys Ala Ala Arg His Arg Thr Pro Ser Leu Arg Ser Pro Asp Gln Pro
305 310 315 320

CCT CCG TGT CCA CAG TTC ATG GCC CAG GGG AAG ACA GGG AGC AGC TCA 1008
Pro Pro Cys Pro Gln Phe Met Ala Gln Gly Lys Thr Gly Ser Ser Ser
325 330 335

CCC CCT GGG GGG CCC CCG AAG CCC GGG AGC CAG CTG GAC AGC ATG CTG 1056
Pro Pro Gly Gly Pro Pro Lys Pro Gly Ser Gln Leu Asp Ser Met Leu
340 345 350

GGG AGC CTG CAG TCT GAC CTG AAC AAG CTG GGG GTC GCC ACA GTC GCC 1104
Gly Ser Leu Gln Ser Asp Leu Asn Lys Leu Gly Val Ala Thr Val Ala
355 360 365

AAA GGA GTC TGC GGG GCC TGC AAG AAG CCC ATC GCC GGG CAG GTT GTG 1152
Lys Gly Val Cys Gly Ala Cys Lys Lys Pro Ile Ala Gly Gln Val Val
370 375 380

ACC GCC ATG GGG AAG ACG TGG CAC CCC GAG CAC TTC GTC TGC ACC CAC 1200
Thr Ala Met Gly Lys Thr Trp His Pro Glu His Phe Val Cys Thr His
385 390 395 400

TGC CAG GAG GAG ATC GGA TCC CGG AAC TTC TTC GAG CGG GAT GGA CAG 1248
Cys Gln Glu Glu Ile Gly Ser Arg Asn Phe Phe Glu Arg Asp Gly Gln
405 410 415

CCC TAC TGT GAA AAG GAC TAC CAC AAC CTC TTC TCC CCG CGC TGC TAC 1296
Pro Tyr Cys Glu Lys Asp Tyr His Asn Leu Phe Ser Pro Arg Cys Tyr
420 425 430

TAC TGC AAC GGC CCC ATC CTG GAT AAA GTG GTG ACA GCC CTT GAC CGG 1344
Tyr Cys Asn Gly Pro Ile Leu Asp Lys Val Val Thr Ala Leu Asp Arg
435 440 445

ACG TGG CAC CCT GAA CAC TTC TTC TGT GCA CAG TGT GGA GCC TTC TTT 1392
Thr Trp His Pro Glu His Phe Phe Cys Ala Gln Cys Gly Ala Phe Phe
450 455 460

GGT CCC GAA GGG TTC CAC GAG AAG GAC GGC AAG GCC TAC TGT CGC AAG 1440
Gly Pro Glu Gly Phe His Glu Lys Asp Gly Lys Ala Tyr Cys Arg Lys
465 470 475 480

GAC TAC TTC GAC ATG TTC GCA CCC AAG TGT GGC GGC TGC GCC CGG GCC 1488
Asp Tyr Phe Asp Met Phe Ala Pro Lys Cys Gly Gly Cys Ala Arg Ala
485 490 495

ATC CTG GAG AAC TAT ATC TCA GCC CTC AAC ACG CTG TGG CAT CCT GAG 1536
Ile Leu Glu Asn Tyr Ile Ser Ala Leu Asn Thr Leu Trp His Pro Glu
500 505 510

TGC TTT GTG TGC CGG GAA TGC TTC ACG CCA TTC GTG AAC GGC AGC TTC 1584
Cys Phe Val Cys Arg Glu Cys Phe Thr Pro Phe Val Asn Gly Ser Phe
515 520 525

TTC GAG CAC GAC GGG CAG CCC TAC TGT GAG GTG CAC TAC CAC GAG CGG 1632
Phe Glu His Asp Gly Gln Pro Tyr Cys Glu Val His Tyr His Glu Arg
530 535 540

CGC GGC TCG CTG TGT TCT GGC TGC CAG AAG CCC ATC ACC GGC CGC TGC 1680
Arg Gly Ser Leu Cys Ser Gly Cys Gln Lys Pro Ile Thr Gly Arg Cys
545 550 555 560

ATC ACC GCC ATG GCC AAG AAG TTC CAC CCC GAG CAC TTC GTC TGT GCC 1728
Ile Thr Ala Met Ala Lys Lys Phe His Pro Glu His Phe Val Cys Ala
565 570 575

TTC TGC CTC AAG CAG CTC AAC AAG GGC ACC TTC AAG GAG CAG AAC GAC 1776
Phe Cys Leu Lys Gln Leu Asn Lys Gly Thr Phe Lys Glu Gln Asn Asp
580 585 590

AAG CCT TAC TGT CAG AAC TGC TTC CTC AAG CTC TTC TGC TAG 1818
Lys Pro Tyr Cys Gln Asn Cys Phe Leu Lys Leu Phe Cys
595 600 605

( 2 ) INFORMATION FOR SEQ ID NO: 7:

( i ) SEQUENCE CHARACTERISTICS:
( A ) LENGTH: 1674 base pairs
( B ) TYPE: nucleic acid
( C ) STRANDEDNESS: double
( D ) TOPOLOGY: linear ( i i ) MOLECULE TYPE: cDNA to mRNA ( i x ) FEATURE:
( A ) NAME/KEY: CDS
( B ) LOCATION:1..1671

( x i ) SEQUENCE DESCRIPTION: SEQ ID NO: 7:

ATG GAC GAC CTC GAC GCC CTG CTG GCG GAC TTG GAG TCT ACC ACC TCC 48
Met Asp Asp Leu Asp Ala Leu Leu Ala Asp Leu Glu Ser Thr Thr Ser
1 5 10 15

CAC ATC TCC AAA CGG CCT GTG TTC TTG TCG GAG GAG ACC CCC TAC TCA 96
His Ile Ser Lys Arg Pro Val Phe Leu Ser Glu Glu Thr Pro Tyr Ser
20 25 30

TAC CCA ACT GGA AAC CAC ACA TAC CAG GAG ATT GCC GTG CCA CCC CCC 144
Tyr Pro Thr Gly Asn His Thr Tyr Gln Glu Ile Ala Val Pro Pro Pro
35 40 45

GTC CCC CCA CCC CCG TCC AGC GAG GCC CTC AAT GGC ACA ATC CTT GAC 192
Val Pro Pro Pro Pro Ser Ser Glu Ala Leu Asn Gly Thr Ile Leu Asp
50 55 60

CCC TTA GAC CAG TGG CAG CCC AGC AGC TCC CGA TTC ATC CAC CAG CAG 240
Pro Leu Asp Gln Trp Gln Pro Ser Ser Ser Arg Phe Ile His Gln Gln
65 70 75 80

CCT CAG TCC TCA TCA CCT GTG TAC GGC TCC AGT GCC AAA ACT TCC AGT 288
Pro Gln Ser Ser Ser Pro Val Tyr Gly Ser Ser Ala Lys Thr Ser Ser
85 90 95

GTC TCC AAC CCT CAG GAC AGT GTT GGC TCT CCG TGC TCC CGA GTG GGT 336
Val Ser Asn Pro Gln Asp Ser Val Gly Ser Pro Cys Ser Arg Val Gly
100 105 110

GAG GAG GAG CAC GTC TAC AGC TTC CCC AAC AAG CAG AAA TCA GCT GAG 384
Glu Glu Glu His Val Tyr Ser Phe Pro Asn Lys Gln Lys Ser Ala Glu
115 120 125

CCT TCA CCC ACC GTA ATG AGC ACG TCC CTG GGC AGC AAC CTT TCT GAA 432
Pro Ser Pro Thr Val Met Ser Thr Ser Leu Gly Ser Asn Leu Ser Glu
130 135 140

CTC GAC CGC CTG CTG CTG GAA CTG AAC GCT GTA CAG CAT AAC CCG CCA 480
Leu Asp Arg Leu Leu Leu Glu Leu Asn Ala Val Gln His Asn Pro Pro
145 150 155 160

GGC TTC CCT GCA GAT GAG GCC AAC TCA AGC CCC CCG CTT CCT GGG GCC 528
Gly Phe Pro Ala Asp Glu Ala Asn Ser Ser Pro Pro Leu Pro Gly Ala

-continued

```
                              165                        170                        175

CTG AGC CCC CTC TAT GGT GTC CCA GAG ACT AAC AGC CCC TTG GGA GGC     576
Leu Ser Pro Leu Tyr Gly Val Pro Glu Thr Asn Ser Pro Leu Gly Gly
            180                 185                 190

AAA GCT GGG CCC CTG ACG AAA GAG AAG CCT AAG CGG AAT GGG GGC CGG     624
Lys Ala Gly Pro Leu Thr Lys Glu Lys Pro Lys Arg Asn Gly Gly Arg
        195                 200                 205

GGC CTG GAG GAC GTG CGG CCC AGT GTG GAG AGT CTC TTG GAT GAA CTG     672
Gly Leu Glu Asp Val Arg Pro Ser Val Glu Ser Leu Leu Asp Glu Leu
    210                 215                 220

GAG AGC TCC GTG CCC AGC CCC GTC CCT GCC ATC ACT GTG AAC CAG GGC     720
Glu Ser Ser Val Pro Ser Pro Val Pro Ala Ile Thr Val Asn Gln Gly
225                 230                 235                 240

GAG ATG AGC AGC CCG CAG CGC GTC ACC TCC ACC CAA CAG CAG ACA CGC     768
Glu Met Ser Ser Pro Gln Arg Val Thr Ser Thr Gln Gln Gln Thr Arg
                245                 250                 255

ATC TCG GCC TCC TCT GCC ACC AGG GAG CTG GAC GAG CTG ATG GCT TCG     816
Ile Ser Ala Ser Ser Ala Thr Arg Glu Leu Asp Glu Leu Met Ala Ser
            260                 265                 270

CTG TCG GAT TTC AAG TTC ATG GCC CAG GGG AAG GCA GGG AGC AGC TCA     864
Leu Ser Asp Phe Lys Phe Met Ala Gln Gly Lys Ala Gly Ser Ser Ser
        275                 280                 285

CCC CCT GGG GGG CCC CCG AAG CCC GGG AGC CAG CTG GAC AGC ATG CTG     912
Pro Pro Gly Gly Pro Pro Lys Pro Gly Ser Gln Leu Asp Ser Met Leu
    290                 295                 300

GGG AGC CTG CAG TCT GAC CTG AAC AAG CTG GGG GTC GCC ACA GTC GCC     960
Gly Ser Leu Gln Ser Asp Leu Asn Lys Leu Gly Val Ala Thr Val Ala
305                 310                 315                 320

AAA GGA GTC TGC GGG GCC TGC AAG AAG CCC ATC GCC GGG CAG GTT GTG    1008
Lys Gly Val Cys Gly Ala Cys Lys Lys Pro Ile Ala Gly Gln Val Val
                325                 330                 335

ACC GCC ATG GGG AAG ACG TGG CAC CCC GAG CAC TTC GTC TGC ACC CAC    1056
Thr Ala Met Gly Lys Thr Trp His Pro Glu His Phe Val Cys Thr His
            340                 345                 350

TGC CAG GAG GAG ATC GGA TCC CGG AAC TTC TTC GAG CGG GAT GGA CAG    1104
Cys Gln Glu Glu Ile Gly Ser Arg Asn Phe Phe Glu Arg Asp Gly Gln
        355                 360                 365

CCC TAC TGT GAA AAG GAC TAC CAC AAC CTC TTC TCC CCG CGC TGC TAC    1152
Pro Tyr Cys Glu Lys Asp Tyr His Asn Leu Phe Ser Pro Arg Cys Tyr
    370                 375                 380

TAC TGC AAC GGC CCC ATC CTG GAT AAA GTG GTG ACA GCC CTT GAC CGG    1200
Tyr Cys Asn Gly Pro Ile Leu Asp Lys Val Val Thr Ala Leu Asp Arg
385                 390                 395                 400

ACG TGG CAC CCT GAA CAC TTC TTC TGT GCA CAG TGT GGA GCC TTC TTT    1248
Thr Trp His Pro Glu His Phe Phe Cys Ala Gln Cys Gly Ala Phe Phe
                405                 410                 415

GGT CCC GAA GGG TTC CAC GAG AAG GAC GGC AAG GCC TAC TGT CGC AAG    1296
Gly Pro Glu Gly Phe His Glu Lys Asp Gly Lys Ala Tyr Cys Arg Lys
            420                 425                 430

GAC TAC TTC GAC ATG TTC GCA CCC AAG TGT GGC GGC TGC GCC CGG GCC    1344
Asp Tyr Phe Asp Met Phe Ala Pro Lys Cys Gly Gly Cys Ala Arg Ala
        435                 440                 445

ATC CTG GAG AAC TAT ATC TCA GCC CTC AAC ACG CTG TGG CAT CCT GAG    1392
Ile Leu Glu Asn Tyr Ile Ser Ala Leu Asn Thr Leu Trp His Pro Glu
    450                 455                 460

TGC TTT GTG TGC CGG GAA TGC TTC ACG CCA TTC GTG AAC GGC AGC TTC    1440
Cys Phe Val Cys Arg Glu Cys Phe Thr Pro Phe Val Asn Gly Ser Phe
465                 470                 475                 480

TTC GAG CAC GAC GGG CAG CCC TAC TGT GAG GTG CAC TAC CAC GAG CGG    1488
Phe Glu His Asp Gly Gln Pro Tyr Cys Glu Val His Tyr His Glu Arg
```

-continued

| | | | | | | | | | | | | | | | | |
|---|---|---|---|---|---|---|---|---|---|---|---|---|---|---|---|---|
| | | | | 485 | | | | | 490 | | | | | 495 | | |
| CGC | GGC | TCG | CTG | TGT | TCT | GGC | TGC | CAG | AAG | CCC | ATC | ACC | GGC | CGC | TGC | 1536 |
| Arg | Gly | Ser | Leu | Cys | Ser | Gly | Cys | Gln | Lys | Pro | Ile | Thr | Gly | Arg | Cys | |
| | | | 500 | | | | | 505 | | | | | 510 | | | |
| ATC | ACC | GCC | ATG | GCC | AAG | AAG | TTC | CAC | CCC | GAG | CAC | TTC | GTC | TGT | GCC | 1584 |
| Ile | Thr | Ala | Met | Ala | Lys | Lys | Phe | His | Pro | Glu | His | Phe | Val | Cys | Ala | |
| | | 515 | | | | | 520 | | | | | 525 | | | | |
| TTC | TGC | CTC | AAG | CAG | CTC | AAC | AAG | GGC | ACC | TTC | AAG | GAG | CAG | AAC | GAC | 1632 |
| Phe | Cys | Leu | Lys | Gln | Leu | Asn | Lys | Gly | Thr | Phe | Lys | Glu | Gln | Asn | Asp | |
| | 530 | | | | | 535 | | | | | 540 | | | | | |
| AAG | CCT | TAC | TGT | CAG | AAC | TGC | TTC | CTC | AAG | CTC | TTC | TGC | TAG | | | 1674 |
| Lys | Pro | Tyr | Cys | Gln | Asn | Cys | Phe | Leu | Lys | Leu | Phe | Cys | | | | |
| 545 | | | | | 550 | | | | | 555 | | | | | | |

ISOFORM GENE FOR FOCAL ADHESION PROTEIN PAXILLIN

FIELD OF THE INVENTION

The present invention relates to a novel gene for an isoform of focal adhesion protein paxillin. The gene of the present invention can be expected to serve for medical applications such as diagnosis of progress of cancer malignancy, development of a drug (cancer treatment) for preventing the metastasis and infiltration of cancer cells, etc.

BACKGROUND OF THE INVENTION

Focal adhesion is not only essential for structuring and maintaining a multicellular organism but is also involved deeply in progress of cancer malignancy, metastasis and infiltration. It is known that paxillin α is located in focal adhesion plaques and interacts with focal adhesion cytoskeletal protein such as vinculin and talin, and signal transducers such as focal adhesion kinase, c-Src tyrosine kinase, Csk, Crk etc., and it appears to play an important part in formation and maintenance of focal adhesion as well as in signal regulation accompanying focal adhesion. Paxillin α reported so far is found to be widely expressed in various cells such as normal tissues and cancer cells such as HeLa etc., and its gene was cloned and sequenced (Salgia et al., Molecular cloning of human paxillin, a focal adhesion protein phosphorylated by p210BCR/ABL, J. Biol. Chem., 270, 5039–5047 (1995)). Moreover, paxillin α is known to bind to focal adhesion kinase, vinculin and talin (Turner et al., Paxillin: a new vinculin-binding protein present in focal adhesions, J. Cell Biol., 111, 1059–1068 (1990); Turner & Miller, Primary sequence of paxillin contains putative SH2 and SH3 domain binding motifs and multiple LIM domains: identification of a vinculin and pp125Fak-binding region, J. Cell Sci., 107, 1583–1592 (1994); Salgia et al., Molecular cloning of human paxillin, a focal adhesion protein phosphorylated by p210BCR/ABL, J. Biol. Chem., 270, 5039–5047 (1995); Hildebrand et al., Paxillin, a tyrosine phosphorylated focal adhesion-associated protein binds to the carboxyl terminal domain of focal adhesion kinase, Mol. Biol. Cell, 6, 637–647 (1995); Tachibana et al., Direct association of pp125FAK with paxillin, the focal adhesion-targeting mechanism of pp125FAK, J. Exp. Med., 182, 1089–1100 (1995)).

SUMMARY OF THE INVENTION

The object of the present invention is to provide a novel gene coding for an isoform of focal adhesion protein paxillin.

As a result of their eager research, the present inventors succeeded in isolating novel isoforms (referred to as paxillins β and γ) of focal adhesion protein paxillin from human monoblastic cell, to complete the present invention.

That is, the present invention is a gene for an isoform (paxillin β) of focal adhesion protein paxillin, coding for an amino acid sequence substantially shown in SEQ ID NO:1; and a gene for an isoform (paxillin γ) of focal adhesion protein paxillin, coding for an amino acid sequence substantially shown in SEQ ID NO:2. Further, the present invention is the gene for paxillin isoform β, having the nucleotide sequence of SEQ ID NO:3; and the gene for paxillin γ, having the nucleotide sequence of SEQ ID NO:4 -(see FIGS. 1A–C and 2A–B and FIGS. 3A–C and 4A–B).

BRIEF DESCRIPTION OF THE DRAWINGS

FIGS. 2A and B shows the (subsequent) amino acid sequence of human paxillin β and its coding nucleotide sequence.

FIGS. 3A to C shows the amino acid sequence of human paxillin γ and its coding nucleotide sequence.

FIGS. 4A and B shows the (subsequent) amino acid sequence of human paxillin γ and its coding nucleotide sequence.

FIGS. 5A to C shows the amino acid sequence of human paxillin α and its coding nucleotide sequence.

FIGS. 6A and B shows the (subsequent) amino acid sequence of human paxillin α and its coding nucleotide sequence.

Lane 1: recombinant viruses (vector only), infected cells (NIH3T3 cells);

Lane 2: recombinant viruses (paxillin α), infected cells (NIH3T3 cells);

Lane 3: recombinant viruses (paxillin α), infected cells (NIH3T3 cells);

Lane 4: recombinant viruses (paxillin γ), infected cells (NIH3T3 cells);

Lane 5: recombinant viruses (vector only), infected cells (3Y1 cells);

Lane 6: recombinant viruses (paxillin., β), infected cells (3Y1 cells)

Lane 7: recombinant viruses (paxillin., α), infected cells (3Y1 cells); and

Lane 8: recombinant viruses (paxillin., γ), infected cells (3Y1 cells).

Figure 9A:
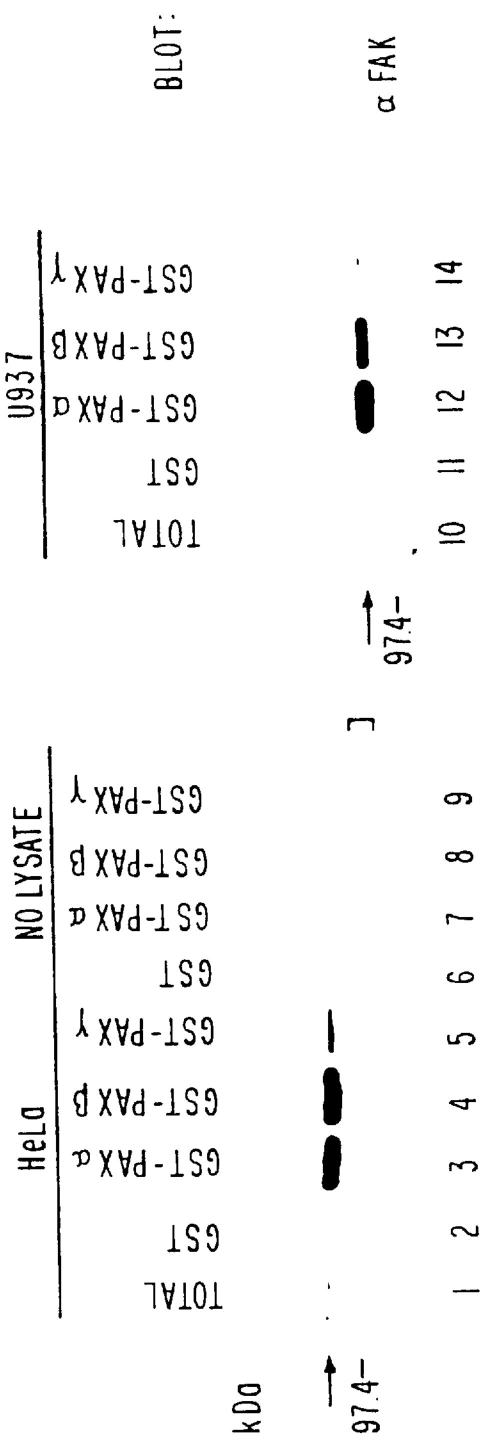
Figure 9B:
Figure 9C:
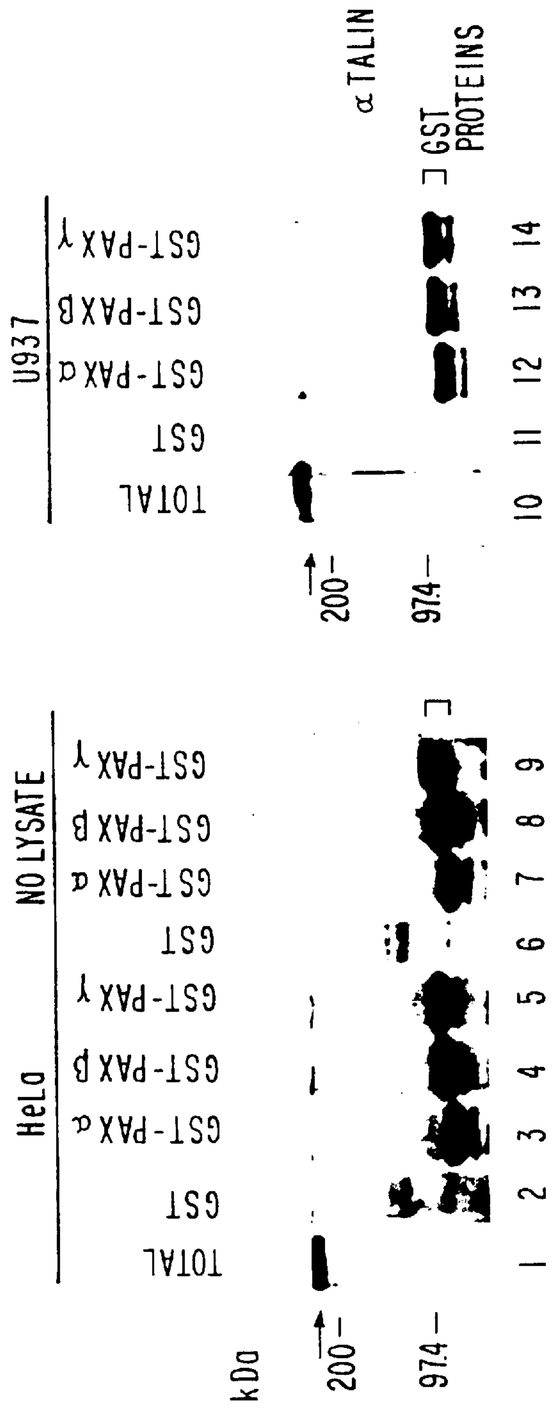

FIGS. 9A to C show the binding characteristics (photograph after electrophoresis) of the paxillin isoform to focal adhesion protein (Fak), vinculin and talin.

Lanes 1 and 10: soluble fractions;

Lanes 1 to 5: cell lysates (prepared from HeLa);

Lanes 6 to 9: control (without cell lysates); and

Lanes 10 to 14: cell lysates (prepared from U937).

Figure 10A:
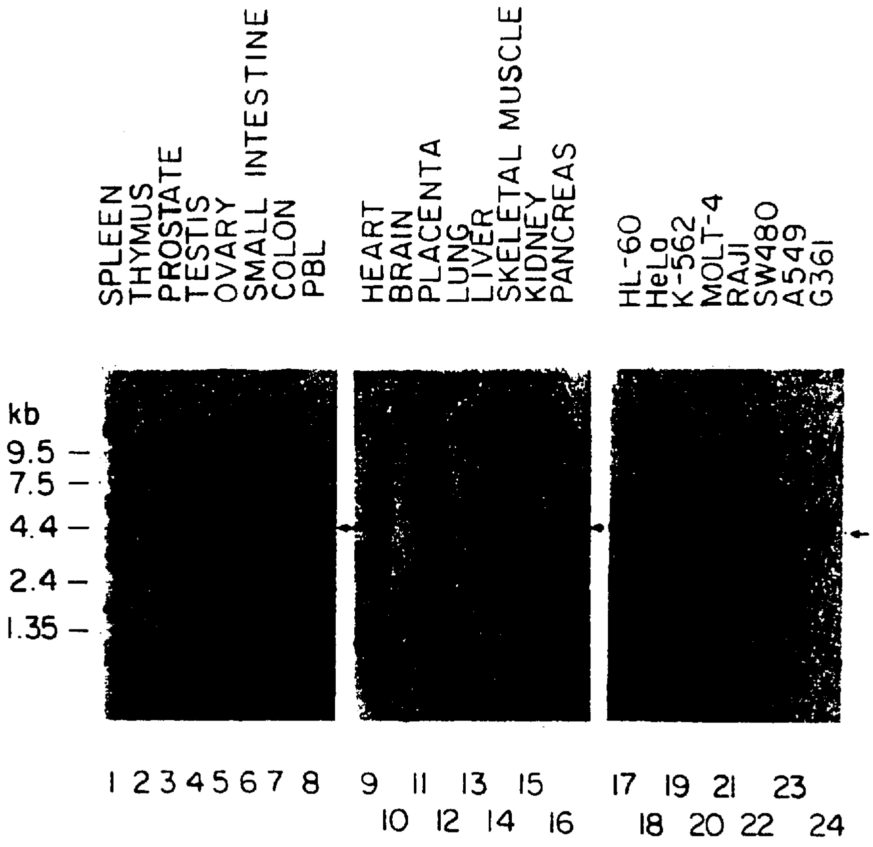
Figure 10B:
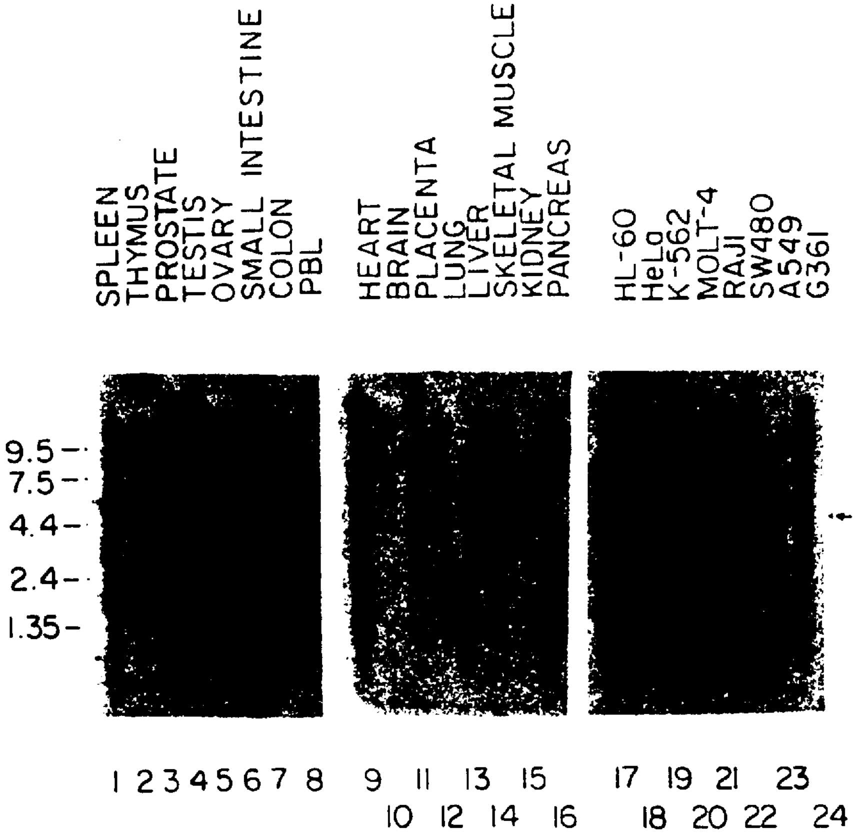
Figure 10C:
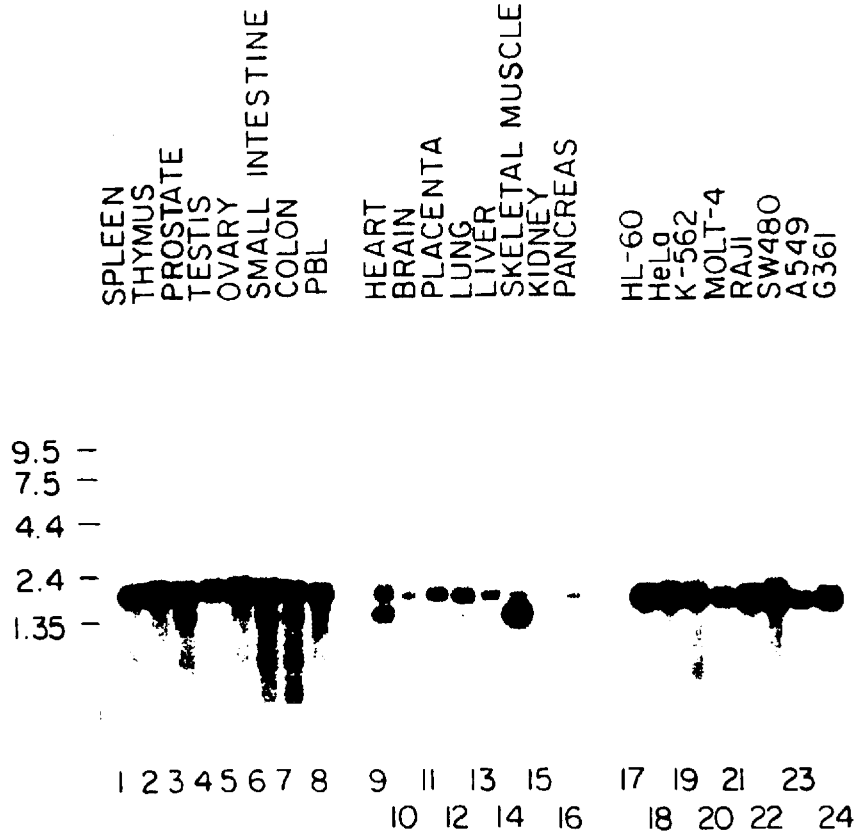

FIGS. 10A to C show the expression of paxillin isoform mRNA in normal tissues and cancer cells (photographs after electrophoresis) [Used probes: (A) paxillin α 1–1072 nucleotide, (B) isoform β-specific probe; and (C) β-actin].

DETAILED DESCRIPTION OF THE INVENTION

Hereinafter, the present invention is described in detail.

As used herein, the term "substantially" means that the amino acid sequences of SEQ ID NOS:1 and 2 may have undergone addition, deletion and/or replacement of 1 or more amino acids insofar the characters of the novel paxillin isoforms are not lost.

cDNAs for the present novel isoforms (paxillins β and γ) of focal adhesion protein paxillin can be isolated by e.g. the method described below in the Examples and their structures can be determined in a usual manner.

The proteins encoded by the 2 paxillin β and γ genes isolated and identified in the present invention have 34 and 48 amino acid insertions, respectively, at the same site (between $Lys^{277}$ and $Phe^{278}$) of previously reported paxillin (paxillin α). Analysis of human genomic structure revealed that each inserted sequence consists of a distinct exon, both of which are found in a 6.4 kb DNA fragment flanked with the 5'- and 3'-coding region of the inserted site. All of these paxillin cDNAs are expressed exogenously in fibroblasts, generating proteins of different sizes, as expected from the cDNA structures. Paxillin β binds to focal adhesion kinase (Fak), but not to vinculin, and paxillin γ binds to vinculin but only weakly to Fak, though both bind to talin, indicating a protein-binding activity distinct from that of known paxillin α.

Moreover, paxillin α mRNA is expressed ubiquitously in normal cells and various cancer cells, while it has been revealed so far that the expression of isoform β mRNA of paxillin is limited to certain types of cancer cells such as SW480 colorectal adenocarcinoma cells, HeLa epithelial carcinoma cells, K562 chronic myelogenous leukemia cells, A549 lung carcinoma cells etc., and that the expression of γ mRNA is limited to only U937 monoblastic cell, so they have distinct expression patterns from that of paxillin α mRNA.

Thus, the novel isoforms of paxillin according to the present invention exhibit distinct protein-binding abilities and expression patterns and can thereby act as distinct molecules involved in focal adhesion and signaling of integrins.

The novel gene for an isoform of focal adhesion protein paxillin according to the present invention can be expected to serve for medical applications such as diagnosis of progress of cancer malignancy, development of a drug (cancer treatment) for preventing the metastasis and infiltration of cancer cells, etc.

EXAMPLES

Hereinafter, the present invention is described in detail with reference to Examples.

The basic operation, enzymatic reaction etc. for DNA recombination were carried out in a usual manner (Sambrook et al., Molecular cloning, a laboratory manual, second edition, Cold Spring Harbor, N.Y., Cold Spring Harbor Laboratory Press (1989)). Unless otherwise specified, the restriction enzymes and various modification enzymes used were products of Takara Shuzo Co., Ltd. The buffer composition and reaction conditions for each enzyme reaction followed the manufacturer's instruction.

Example 1

Isolation and Identification of Paxillin Isoform Gene (1) Isolation of CDNA

Standard methods (Sambrook et al. (1989) supra) were used for DNA and RNA manipulations, unless otherwise stated.

According to the manufacturer's instruction (Quick Prep mRNA purification kit, Pharmacia), polyadenylated RNA was prepared from human monoblastic cell U937 cultured in RPMI 1640 medium supplemented with 10% sterilized FCS, and cDNA was synthesized from poly (A) mRNA templates using random primers and reverse transcriptase (Pharmacia).

(2) PCR Amplification of Human Paxillin Transcripts

On the basis of the reported cDNA sequence for human paxillin isoform α (Salgia et al., Molecular cloning of human paxillin, a focal adhesion protein phosphorylated by p210 BCR/ABL, J. Biol. Chem., 270, 5039–5047 (1995): see FIGS. 5A–C and 6A–B, the following oligonucleotide primers were synthesized.

Nucleotide numbers in the present invention correspond to the sequence of human paxillin isoform α, with nucleotide A at the first ATG codon as number 1.

Primer 1 (1 to 24) : 5'-CCGGATCCATGGACGACCTCGACGCCCTGCTG-3'

Primer 2 (922 to 942) : 5'-CAGCTTGTTCAGGTCAGACTG-3'

Primer 3 (844 to 865) : 5'-GGGAAGACAGGGAGCAGCTCAC-3'

Primer 4 (1648 to 1674): 5'-CCGAATTCCTAGCAGAAGAGCTTGAGGAAGCAGTT-3'

PCR amplification of human paxillin transcripts was performed using a combination of primers 1 and 2 or primers 3 and 4. After digestion of the former PCR products with BamHI and SphI (located at nucleotide 905 of isoform α), and the latter with SphI and EcoRI, these DNA fragments were ligated with BamHI-EcoRI cleaved pGEX-2T vector (Pharmacia) using T4 DNA ligase (Takara Shuzo Co., Ltd.). The resulting plasmids were transformed into Escherichia coli DH5, and each clone was isolated and subjected to DNA sequencing analysis.

(3) DNA Sequencing Analysis

Figure 7A:
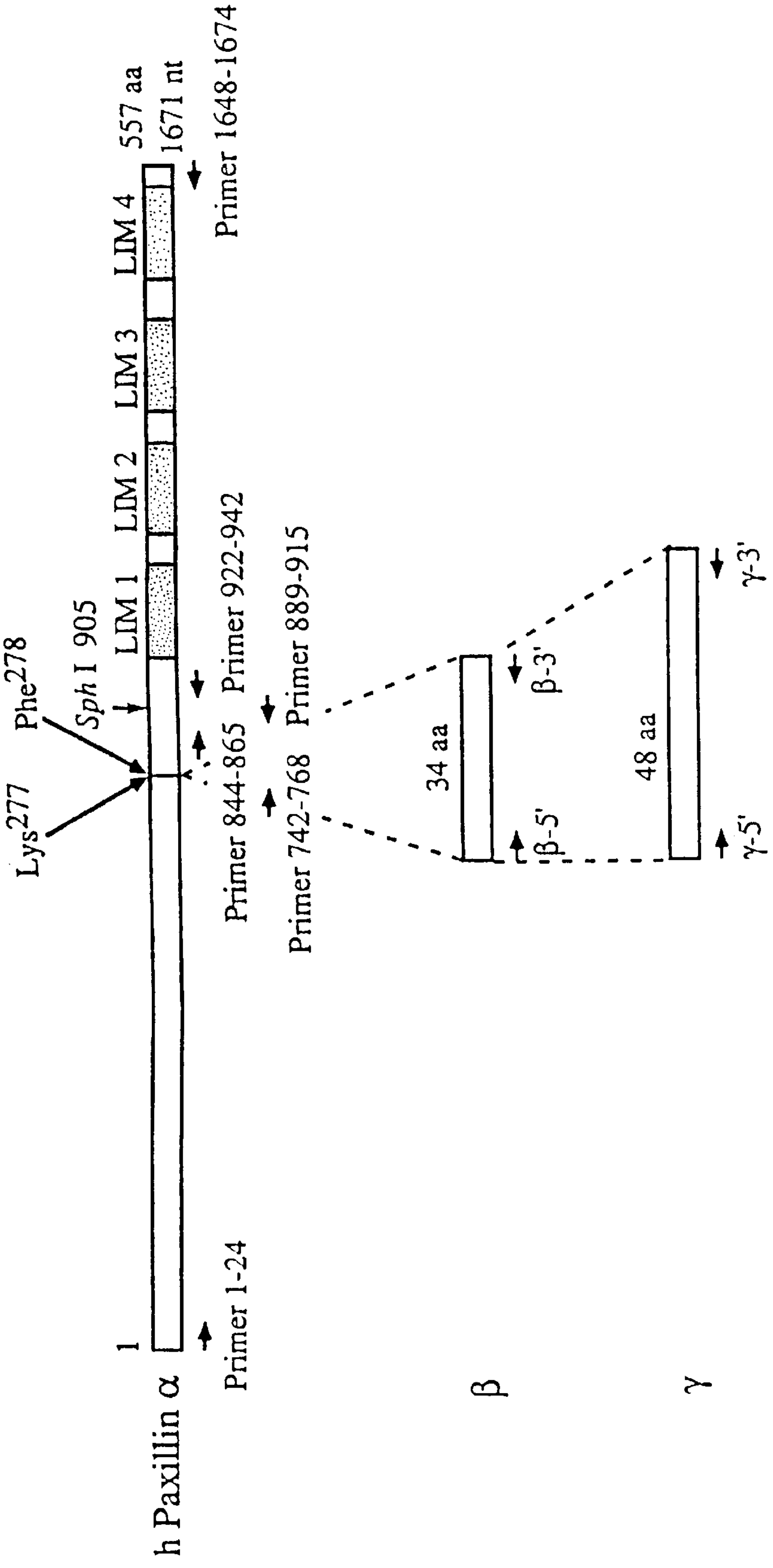
FIGS. 7A, B1 and B2 show the structures of cDNA for human paxillin α and genomic DNA containing human β- and γ-specific exons.
Figures 1, 7B:
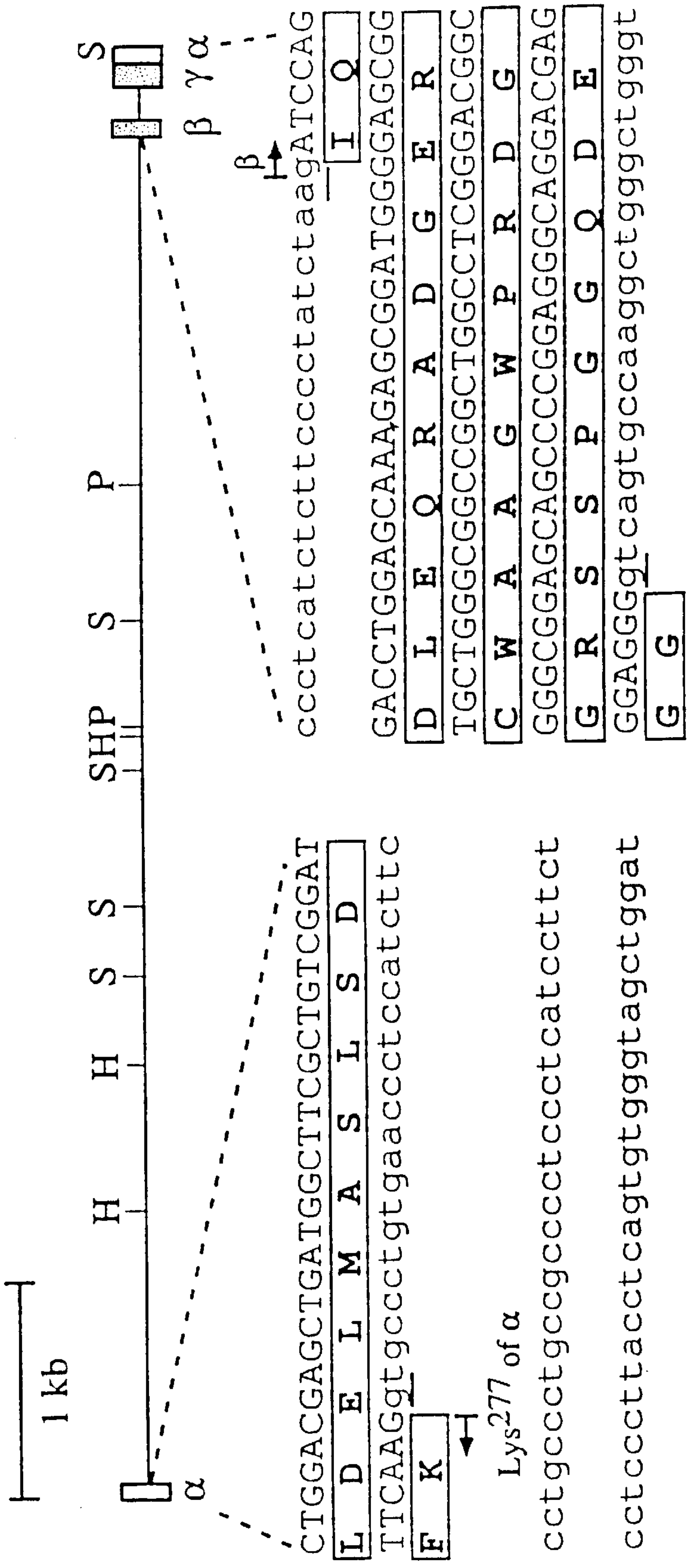
FIGS. 1A to C shows the amino acid sequence of human paxillin β and its coding nucleotide sequence.

Two of four isolated paxillin cDNA clones were found to have additional sequences to the previously reported paxillin α cDNA sequence (Salgia et al. (1989) supra: FIGS. 7B1–B2)). Both of the additional sequences were inserted at the same site (just after amino acid $Lys^{277}$, i.e. between nucleotides 831 and 832) of the reported paxillin sequences (FIG. 7 (A)). Both of the inserted sequences were linked in frame to both the 3'-end and 5'-end of the flanking sequences of paxillin α cDNA. Except for these inserted sequences, both cDNAs showed the same sequences as that previously reported for paxillin α. The isoforms encoded by the longer cDNAs having the inserted sequences are referred to hereinafter as isoforms β and γ, respectively. Isoform β contained a 34 amino acid insert, and isoform γ contained a 48 amino acid insert (FIG. 7 (B)).

(4) Isolation of a Genomic DNA Fragment of Paxillin

High molecular weight DNA isolated from human placental tissue was subjected to PCR amplification using the following oligonucleotide primes synthesized on the basis of sequences before and after the above inserted sequences:

Primer 5 (742 to 768): 5'-GTCACCTCCACCCAACAGCAGACACGC-3'; and

Primer 6 (889 to 915): 5'-CCCCAGCATGCTGTCCAGCTGGCTCCC-3', whereby a genomic DNA fragment was obtained as a single DNA band of 6.4 kb in length.

The 6.4 kb DNA fragment was isolated from the gel and then ligated into pT7 Blue (R) vector bearing single 3'T overhangs at its EcoRV site (Novagen). After transformation of the resulting plasmid into Escherichia coli NovaBlue cells (Novagen), a single clone was isolated and subjected to restriction enzyme mapping and sequencing analysis.

As shown in FIGS. 7B1–B2, just after the sequences corresponding to the codon for $Lys^{277}$ of paxillin α , there began an about 6 kb intron, thereafter an exon encoding the inserted sequence of isoform β, an intron of 142 nucleotides in length, and another exon encoding the inserted sequence of isoform γ. The latter exon was connected directly to the coding region of $Phe^{278}$ and thereafter of paxillin α sequences.

Example 2

Expression of Paxillin Isoforms in Fibroblasts BglI-EcoRI fragments of each paxillin isoform were isolated from the pGEX-2T constructs and then ligated into a synthetic double-stranded DNA fragment containing the 5'-end coding region as well as the Kozak sequences (underlined) of paxillin (Salgia et al. (1995) supra):

5'-GATCTCCGGCCATGGACGACCTCGACGCCCTGC-3'

3'-AGGCCGGTACCTGCTGGAGCTGCGGG-5'

The ligated fragments were further ligated into BamHI- and EcoRI-cleaved pBabePuro vector (Morgenstern et al., Advanced mammalian gene transfer; high titer retrovial vector with multiple drug selection markers and a complementary helper-free packaging cell line, Nucleic Acids Res., 18, 3587–3596 (1990)). After isolation of single clones with each isoform, constructs were confirmed by sequencing analysis.

The resulting plasmid DNAs were transfected into BOSC23 virus-packaging cells by the calcium-phosphate precipitation method (Pear et al., Production of higher-titer helper-free retroviruses by transient transfection, Proc. Natl. Acad. Sci. USA 90, 8392–8396 (1993)), and 48 hours after transfection, recombinant viruses bearing pBabePuro/paxillins were collected. Fibroblasts NIH3T3 and 3Y1 cells were then infected with these viruses. After culturing the infected cells for one week in the presence of 2 μg/ml puromycin (Sigma), the cells were harvested and analyzed for expression of paxillin by immunoblotting using anti-paxillin antibodies separately prepared by immunizing rabbits with a Keyhole limpet hemocyanin-conjugated synthetic peptide of amino acids 199 to 217 of isoform α sequence.

Figure 8:
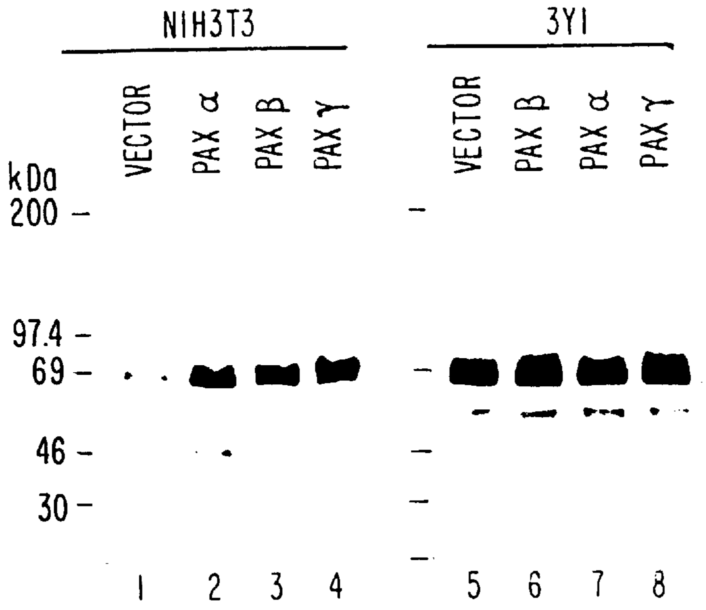
FIG. 8 shows the exogenous expression (photograph after electrophoresis) of the paxillin isoform in fibroblasts.

As shown in FIG. 8, a protein of the expected size reacting with polyclonal anti-paxillin antibodies was detected in both kinds of infected cells. Exogenous expression of the paxillin isoforms was detected over the endogenous protein in mouse NIH3T3 cells. On the other hand, little increase in the amounts of paxillin was seen in the infected rat 3Y1 cells, where the amount of endogenous paxillin appeared to be more than several fold greater than that of NIH3T3 cells.

Example 3

Binding Characteristics of Paxillin Isoforms (1) Preparation of Paxillin Isoform-GST Fusion Protein pGEX-2T vectors containing cDNA sequences coding respectively for the human paxillin isoforms α, β and γ were expressed in Escherichia coli as glutathione-S-transferase (GST) fusion proteins by isopropyl-β-D-thiogalactopyranoside induction. The fusion proteins were expressed in E. coli in a usual manner, and the cells were lyzed and coupled to glutathione beads.

Cell lysates were prepared at 4° C. by lyzing HeLa cells and U937 cells with 1% NP-40 buffer and clarifying them for 10 minutes with $10^4$×g. Each 500 μg of lysates was incubated with 5 μg of the GST-fusion proteins bound to glutathione-Sepharose beads at 4° C. for 2 hours. The beads were then washed extensively with 1% NP-40 buffer (1% NP-40, 150 mM NaCl, 20 mM Tris-HCl (pH 7.4), 5 mM EDTA, 1 mM phenylmethylsulfonyl fluoride, 1% aprotinin and 2μg/ml leupeptin).

(2) Protein Binding Assay

Cell proteins (co-precipitated with the GST-fusion proteins) recovered with the beads in the above operation were analyzed as follows: The proteins were separated by 7.5% SDS-PAGE and transferred to membrane filters (Immobilin P, Millipore). After blocking with Tris-buffered saline containing 0.1% Tween 20 (Sigma) and 5% BSA (Sigma), filter membranes were probed with antibodies to various cell proteins (anti-talin antibody (8d4, Sigma Immuno Chemicals) and anti-vinculin antibody (VIN-11-5, Sigma Immuno Chemicals) or anti-Fak antibody (Transduction Lab.)). The antibodies retained on filter membranes were then detected by peroxidase-conjugated secondary antibody (Jackson ImmunoResearch Lab.) and visualized by an enzyme-linked chemiluminescence method according to the manufacturer's instruction (Amersham).

Isoform α has been reported to bind to Fak, talin and vinculin, and in this example too, these focal adhesion proteins were co-precipitated with the GST-fusion protein of paxillin α. In contrast, the β and γ isoforms co-precipitated different amounts of these focal adhesion proteins. Compared to the binding of isoform α, isoform β binds to Fak and talin but not to vinculin; isoform γ binds to vinculin ,-A4 and talin but only weakly binds to Fak (FIGS. 9A–C).

Example 4 mRNA Expression of Paxillins α, β and γ

Expression of paxillins α, β and γ were examined by Northern blotting using multiple tissue blotting as well as cancer cell blotting (Clontech).

The results are shown in FIGS. 10A–C. Paxillin α mRNA was expressed ubiquitously in most normal tissues (spleen, thymus, prostate, testis, ovary, small intestine, colon, PBL, heart, brain, placenta, lung, liver, skeletal muscle, kidney and pancreas). Among cancer cells examined, α mRNA was expressed at high levels in HeLa epithelial carcinoma cells, K562 chronic myelogenous leukemia cells, SW480 colorectal adenocarcinoma cells, A549 lung carcinoma cells and G361 melanoma cells, and marginal levels of the expression were detected in Molt 4 lymphoblastic leukemia cells and Raji Burkitt's lymphoma cells. The expression of α mRNA was not detected in HL-60 promyelocytic leukemia cells (FIG. 10 (A)).

On the other hand, the expression of paxillin β and γ mRNAs were not detected in any of the normal tissues. β mRNA, however, was expressed at a high level in SW480 cells, with low levels in HeLa cells, K562 cells, and A549 cells, but the expression was not detected in HL-60, Molt 4 cells, Raji cells and G361 cells (FIG. 10 (B)). γ mRNA was not detected in any of the above cell lines, and as confirmed in Example 1, its expression was detected in only U937 monoblastic cell.

What is claimed is:

1. An isolated nucleic acid molecule for an isoform (paxillin β) of focal adhesion protein paxillin, coding for an amino acid sequence substantially shown in SEQ ID NO:1.

2. An isolated nucleic acid molecule for an isoform (paxillin γ) of focal adhesion protein paxillin, coding for an amino acid sequence substantially shown in SEQ ID NO:2.

3. The isolated nucleic acid molecule for an isoform (paxillin β) of focal adhesion protein paxillin according to claim 1, having the nucleotide sequence of SEQ ID NO:3.

4. The isolated nucleic acid molecule for an isoform (paxillin γ) of focal adhesion protein paxillin according to claim 2, having the nucleotide sequence of SEQ ID NO:4.

5. A focal adhesion protein paxillin (paxillin β) having an amino acid sequence substantially shown in SEQ ID NO:1.

6. A focal adhesion protein paxillin (paxillin γ) having an amino acid sequence substantially shown in SEQ ID NO:2.

7. The isolated nucleic acid molecule according to claim 1, wherein said nucleic acid molecule is selected from the group consisting of genomic DNA, cDNA and mRNA.

8. The isolated nucleic acid molecule according to claim 2, wherein said nucleic acid molecule is selected from the group consisting of genomic DNA, cDNA and mRNA.

9. The isolated nucleic acid molecule according to claim 3, wherein said nucleic acid molecule is selected from the group consisting of genomic DNA, cDNA and mRNA.

10. The isolated nucleic acid molecule according to claim 4, wherein said nucleic acid molecule is selected from the group consisting of genomic DNA, cDNA and mRNA.

11. An expression vector comprising the isolated nucleic acid molecule of claim 3 operably linked to a promoter.

12. An expression vector comprising the isolated nucleic acid molecule of claim 4 operably linked to a promoter.

13. A host cell transfected by the expression vector of claim 11.

14. A host cell transfected by the expression vector of claim 12.

15. A fusion protein comprising the protein according to claim 5.

16. A fusion protein comprising the protein according to claim 6.

17. A method for detecting paxillin β, in a sample comprising:

contacting said sample specific for paxillin β, with a first antibody specific for said paxillin β under conditions favoring binding of said paxillin β to said first antibody, wherein binding of said first antibody to said paxillin β is indicative of the presence of said paxillin β in said sample.

18. The method according to claim 17, wherein said first antibody is labelled.

19. The method according to claim 17, further comprising a second antibody specific for said first antibody.

* * * * *